United States Patent
Dong et al.

(10) Patent No.: US 12,275,951 B2
(45) Date of Patent: *Apr. 15, 2025

(54) ENGINEERED GUIDE RNA AND USES THEREOF

(71) Applicant: Ohio State Innovation Foundation, Columbus, OH (US)

(72) Inventors: Yizhou Dong, Dublin, OH (US); Bin Li, Columbus, OH (US)

(73) Assignee: Ohio State Innovation Foundation, Columbus, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/269,021

(22) Filed: Feb. 6, 2019

(65) Prior Publication Data

US 2019/0241911 A1     Aug. 8, 2019

Related U.S. Application Data

(60) Provisional application No. 62/626,827, filed on Feb. 6, 2018.

(51) Int. Cl.
| | |
|---|---|
| *C12N 15/90* | (2006.01) |
| *A61K 31/7105* | (2006.01) |
| *A61K 31/712* | (2006.01) |
| *A61K 31/7125* | (2006.01) |
| *C12N 9/22* | (2006.01) |
| *C12N 15/85* | (2006.01) |

(52) U.S. Cl.
CPC ........ *C12N 15/907* (2013.01); *A61K 31/7105* (2013.01); *A61K 31/712* (2013.01); *A61K 31/7125* (2013.01); *C12N 9/22* (2013.01); *C12N 15/85* (2013.01); *C12N 2310/122* (2013.01); *C12N 2310/20* (2017.05); *C12N 2310/315* (2013.01); *C12N 2310/3235* (2013.01); *C12N 2310/333* (2013.01); *C12N 2310/3341* (2013.01); *C12N 2310/335* (2013.01)

(58) Field of Classification Search
None
See application file for complete search history.

(56) References Cited

U.S. PATENT DOCUMENTS

| | | | |
|---|---|---|---|
| 9,790,490 B2 * | 10/2017 | Zhang | C12N 9/22 |
| 12,065,667 B2 * | 8/2024 | Dong | C12N 15/85 |
| 2016/0208243 A1 * | 7/2016 | Zhang | C12N 15/85 |
| 2019/0233814 A1 * | 2/2019 | Zhang | C12N 15/902 |

OTHER PUBLICATIONS

Pallan et al., "Unexpected origins of the enhanced pairing affinity of 2'-fluoro-modified RNA" 39(8) Nucleic Acids Research 3482-3495 (Year: 2010).*
Fonfara et al., "The CRISPR-associated DNA-cleaving enzyme Cpf1 also processes precursor CRISPR RNA" 532 Nature 517-535 (Year: 2016).*
Li et al., "Engineering CRISPR-Cpf1 crRNAs and mRNAs to maximize genome editing efficiency" 1(5) Nature Biomedical Engineering Article 0066 1-10 (Year: 2017).*
Latorre et al., "Modified RNAs in CRISPR/Cas9: An Old Trick" 55 Angewandte Chemie 3548-3550 (Year: 2016).*
Li et al., "Engineering CRISPR-Cpf1 crRNAs and mRNAs to maximize genome editing efficiency" 1(5) Nature Biomedical Engineering Article 0066 Supplemental Material (Year: 2017).*
Hendel et al., "Chemically modified guide RNAs enhance CRISPR-Cas genome editing in human primary cells" 33(9) Nature Biotechnology 985-909/Methods (Year: 2015).*
Rahdar et al., "Synthetic CRISPR RNA-Cas9-guided genome editing in human cells" 112 Proceedings of the National Academy of Sciences USA E7110-E7117 (Year: 2015).*
Li et al., "Engineering CRISPR-Cpf1 crRNAs and mRNAs to maximize genome editing efficiency" 1 Nature Biomedical Engineering 0066: 1-10 (Year: 2017).*
Altschul et al. (1977) Nuc. Acids Res. 25:3389-3402.
Altschul et al. (1990) J. Mol. Biol. 215:403-410.
Beaucage and Carruthers, (1981) Tetrahedron Lett., 22:1859-1862.
Boshart et al., (1985) Cell, 41:521-530.
Henikoff and Henikoff (1989) Proc. Natl. Acad. Sci. USA 89:10915.
Karlin and Altschul (1993) Proc. Natl. Acad. Sci. USA 90:5873-5787.
Matteucci, et al., (1981) J. Am. Chem. Soc., 103:3185.
Takebe, et al., (1988) Mol. Cell. Biol., vol. 8(1), p. 466-472.
O'Hare, et al., (1981) Proc. Natl. Acad. Sci. USA., vol. 78(3), p. 1527-31.
Zetsche, B. et al. (2015) Cpf1 is a single RNA-guided endonuclease of a class 2 CRISPR-Cas system. Cell. 163(3):759-71.

* cited by examiner

*Primary Examiner* — Nancy J Leith
(74) *Attorney, Agent, or Firm* — Meunier Carlin & Curfman LLC

(57) ABSTRACT

The present disclosure generally relates to systems, methods and compositions for use in Clustered Regularly Interspaced Short Palindromic Repeats (CRISPR)-Cpf1 genome editing systems.

4 Claims, 7 Drawing Sheets

Specification includes a Sequence Listing.

SEQUENCE LISTING

```
<160> NUMBER OF SEQ ID NOS: 80

<210> SEQ ID NO 1
<211> LENGTH: 65
<212> TYPE: RNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)..(5)
<223> OTHER INFORMATION: optional random nucleotides
<220> FEATURE:
<221> NAME/KEY: misc_feature
<222> LOCATION: (42)..(64)
<223> OTHER INFORMATION: guide segment
<220> FEATURE:
<221> NAME/KEY: misc_feature
<222> LOCATION: (65)..(65)
<223> OTHER INFORMATION: optional 3'-extension

<400> SEQUENCE: 1
nnnnngucua agaacuuuaa auaauuucua cuguuguaga unnnnnnnnn nnnnnnnnnn      60 nnnnn                                                                 65

<210> SEQ ID NO 2
<211> LENGTH: 65
<212> TYPE: RNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)..(5)
<223> OTHER INFORMATION: optional random nucleotides
<220> FEATURE:
<221> NAME/KEY: misc_feature
<222> LOCATION: (42)..(64)
<223> OTHER INFORMATION: guide segment
```

```
<220> FEATURE:
<221> NAME/KEY: misc_feature
<222> LOCATION: (65)..(65)
<223> OTHER INFORMATION: optional 3'-extension

<400> SEQUENCE: 2
nnnnnguuuu ggaguaccuu agaaaugcau gguucucaug cnnnnnnnnn nnnnnnnnnn    60 nnnnn                                                                65

<210> SEQ ID NO 3
<211> LENGTH: 64
<212> TYPE: RNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)..(5)
<223> OTHER INFORMATION: optional random nucleotides
<220> FEATURE:
<221> NAME/KEY: misc_feature
<222> LOCATION: (41)..(63)
<223> OTHER INFORMATION: guide segment
<220> FEATURE:
<221> NAME/KEY: misc_feature
<222> LOCATION: (64)..(64)
<223> OTHER INFORMATION: optional 3'-extension

<400> SEQUENCE: 3
nnnnnguuuu agaaccuuaa aaauuaccua guaauuaggu nnnnnnnnnn nnnnnnnnnn    60 nnnn                                                                 64

<210> SEQ ID NO 4
<211> LENGTH: 65
<212> TYPE: RNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)..(5)
<223> OTHER INFORMATION: optional random nucleotides
<220> FEATURE:
<221> NAME/KEY: misc_feature
<222> LOCATION: (42)..(64)
<223> OTHER INFORMATION: guide segment
<220> FEATURE:
<221> NAME/KEY: misc_feature
<222> LOCATION: (65)..(65)
<223> OTHER INFORMATION: optional 3'-extension

<400> SEQUENCE: 4
nnnnnguuua aaaguccuau uggauuucua cuuuuguaga unnnnnnnnn nnnnnnnnnn    60 nnnnn                                                                65

<210> SEQ ID NO 5
<211> LENGTH: 65
<212> TYPE: RNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)..(5)
<223> OTHER INFORMATION: optional random nucleotides
<220> FEATURE:
<221> NAME/KEY: misc_feature
<222> LOCATION: (42)..(64)
<223> OTHER INFORMATION: guide segment
<220> FEATURE:
```

```
<221> NAME/KEY: misc_feature
<222> LOCATION: (65)..(65)
<223> OTHER INFORMATION: optional 3'-extension

<400> SEQUENCE: 5
nnnnngccaa auaccucuau aaaauuucua cuuuuguaga unnnnnnnnn nnnnnnnnn      60 nnnnn                                                                65

<210> SEQ ID NO 6
<211> LENGTH: 61
<212> TYPE: RNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)..(5)
<223> OTHER INFORMATION: optional random nucleotides
<220> FEATURE:
<221> NAME/KEY: misc_feature
<222> LOCATION: (38)..(60)
<223> OTHER INFORMATION: guide segment
<220> FEATURE:
<221> NAME/KEY: misc_feature
<222> LOCATION: (61)..(61)
<223> OTHER INFORMATION: optional 3'-extension

<400> SEQUENCE: 6
nnnnnguuuc aauccacgcg cccacgcggg gcgcgacnnn nnnnnnnnnn nnnnnnnnn       60 n                                                                    61

<210> SEQ ID NO 7
<211> LENGTH: 64
<212> TYPE: RNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)..(5)
<223> OTHER INFORMATION: optional random nucleotides
<220> FEATURE:
<221> NAME/KEY: misc_feature
<222> LOCATION: (41)..(63)
<223> OTHER INFORMATION: guide segment
<220> FEATURE:
<221> NAME/KEY: misc_feature
<222> LOCATION: (64)..(64)
<223> OTHER INFORMATION: optional 3'-extension

<400> SEQUENCE: 7
nnnnngucaa aagaccuuuu uaauuucuac ucuuguagau nnnnnnnnnn nnnnnnnnn       60 nnnn                                                                 64

<210> SEQ ID NO 8
<211> LENGTH: 65
<212> TYPE: RNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)..(5)
<223> OTHER INFORMATION: optional random nucleotides
<220> FEATURE:
<221> NAME/KEY: misc_feature
<222> LOCATION: (42)..(64)
<223> OTHER INFORMATION: guide segment
<220> FEATURE:
<221> NAME/KEY: misc_feature
```

```
<222> LOCATION: (65)..(65)
<223> OTHER INFORMATION: optional 3'-extension

<400> SEQUENCE: 8
nnnnngcuua gaacauuuaa agaauuucua cuauuguaga unnnnnnnnn nnnnnnnnnn      60 nnnnn                                                                 65

<210> SEQ ID NO 9
<211> LENGTH: 64
<212> TYPE: RNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)..(5)
<223> OTHER INFORMATION: optional random nucleotides
<220> FEATURE:
<221> NAME/KEY: misc_feature
<222> LOCATION: (41)..(63)
<223> OTHER INFORMATION: guide segment
<220> FEATURE:
<221> NAME/KEY: misc_feature
<222> LOCATION: (64)..(64)
<223> OTHER INFORMATION: optional 3'-extension

<400> SEQUENCE: 9
nnnnncucaa aacucauucg aaucucuacu cuuuguagau nnnnnnnnnn nnnnnnnnnn      60 nnnn                                                                  64

<210> SEQ ID NO 10
<211> LENGTH: 65
<212> TYPE: RNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)..(5)
<223> OTHER INFORMATION: optional random nucleotides
<220> FEATURE:
<221> NAME/KEY: misc_feature
<222> LOCATION: (42)..(64)
<223> OTHER INFORMATION: guide segment
<220> FEATURE:
<221> NAME/KEY: misc_feature
<222> LOCATION: (65)..(65)
<223> OTHER INFORMATION: optional 3'-extension

<400> SEQUENCE: 10
nnnnnguuug aauaaccuua aauaauuucu acuuuguaga unnnnnnnnn nnnnnnnnnn      60 nnnnn                                                                 65

<210> SEQ ID NO 11
<211> LENGTH: 65
<212> TYPE: RNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)..(5)
<223> OTHER INFORMATION: optional random nucleotides
<220> FEATURE:
<221> NAME/KEY: misc_feature
<222> LOCATION: (42)..(64)
<223> OTHER INFORMATION: guide segment
<220> FEATURE:
<221> NAME/KEY: misc_feature
<222> LOCATION: (65)..(65)
```

<223> OTHER INFORMATION: optional 3'-extension

<400> SEQUENCE: 11
nnnnngucua acgaccuuuu aaauuucuac uguuuguaga unnnnnnnnn nnnnnnnnn    60 nnnnn                                                               65

<210> SEQ ID NO 12
<211> LENGTH: 65
<212> TYPE: RNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)..(5)
<223> OTHER INFORMATION: optional random nucleotides
<220> FEATURE:
<221> NAME/KEY: misc_feature
<222> LOCATION: (42)..(64)
<223> OTHER INFORMATION: guide segment
<220> FEATURE:
<221> NAME/KEY: misc_feature
<222> LOCATION: (65)..(65)
<223> OTHER INFORMATION: optional 3'-extension

<400> SEQUENCE: 12
nnnnncucua aagagaggaa agaauuucua cuuuuguaga unnnnnnnnn nnnnnnnnn    60 nnnnn                                                               65

<210> SEQ ID NO 13
<211> LENGTH: 65
<212> TYPE: RNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)..(5)
<223> OTHER INFORMATION: optional random nucleotides
<220> FEATURE:
<221> NAME/KEY: misc_feature
<222> LOCATION: (42)..(64)
<223> OTHER INFORMATION: guide segment
<220> FEATURE:
<221> NAME/KEY: misc_feature
<222> LOCATION: (65)..(65)
<223> OTHER INFORMATION: optional 3'-extension

<400> SEQUENCE: 13
nnnnnguuuc aaagauuaaa uaauuucuac uaaguguaga unnnnnnnnn nnnnnnnnn    60 nnnnn                                                               65

<210> SEQ ID NO 14
<211> LENGTH: 65
<212> TYPE: RNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)..(5)
<223> OTHER INFORMATION: optional random nucleotides
<220> FEATURE:
<221> NAME/KEY: misc_feature
<222> LOCATION: (42)..(64)
<223> OTHER INFORMATION: guide segment
<220> FEATURE:
<221> NAME/KEY: misc_feature
<222> LOCATION: (65)..(65)
<223> OTHER INFORMATION: optional 3'-extension

```
<400> SEQUENCE: 14
nnnnngucua gguacucucu uuaauuucua cuauuguaga unnnnnnnnn nnnnnnnnn    60 nnnnn                                                                65

<210> SEQ ID NO 15
<211> LENGTH: 65
<212> TYPE: RNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)..(5)
<223> OTHER INFORMATION: optional random nucleotides
<220> FEATURE:
<221> NAME/KEY: misc_feature
<222> LOCATION: (42)..(64)
<223> OTHER INFORMATION: guide segment
<220> FEATURE:
<221> NAME/KEY: misc_feature
<222> LOCATION: (65)..(65)
<223> OTHER INFORMATION: optional 3'-extension

<400> SEQUENCE: 15
nnnnngucaa uaagacucau uuaauuucua cuucgguaga unnnnnnnnn nnnnnnnnn    60 nnnnn                                                                65

<210> SEQ ID NO 16
<211> LENGTH: 65
<212> TYPE: RNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)..(5)
<223> OTHER INFORMATION: optional random nucleotides
<220> FEATURE:
<221> NAME/KEY: misc_feature
<222> LOCATION: (42)..(64)
<223> OTHER INFORMATION: guide segment
<220> FEATURE:
<221> NAME/KEY: misc_feature
<222> LOCATION: (65)..(65)
<223> OTHER INFORMATION: optional 3'-extension

<400> SEQUENCE: 16
nnnnngccua uaaggcuuua guaauuucua cuauuguaga unnnnnnnnn nnnnnnnnn    60 nnnnn                                                                65

<210> SEQ ID NO 17
<211> LENGTH: 36
<212> TYPE: RNA
<213> ORGANISM: Artificial Sequence
<220> FEATURE:
<223> OTHER INFORMATION: synthetic construct

<400> SEQUENCE: 17
gucuaagaac uuuaaauaau uucuacuguu guagau                              36

<210> SEQ ID NO 18
<211> LENGTH: 36
<212> TYPE: RNA
<213> ORGANISM: Artificial Sequence
<220> FEATURE:
<223> OTHER INFORMATION: synthetic construct
```

<400> SEQUENCE: 18
guuuuggagu accuuagaaa ugcauggzuc ucaugc                36

<210> SEQ ID NO 19
<211> LENGTH: 35
<212> TYPE: RNA
<213> ORGANISM: Artificial Sequence
<220> FEATURE:
<223> OTHER INFORMATION: synthetic construct

<400> SEQUENCE: 19
guuuuagaac cuuaaaaauu accuaguaau uaggu                 35

<210> SEQ ID NO 20
<211> LENGTH: 36
<212> TYPE: RNA
<213> ORGANISM: Artificial Sequence
<220> FEATURE:
<223> OTHER INFORMATION: synthetic construct

<400> SEQUENCE: 20
guuuaaaagu ccuauuggau uucuacuuuu guagau                36

<210> SEQ ID NO 21
<211> LENGTH: 36
<212> TYPE: RNA
<213> ORGANISM: Artificial Sequence
<220> FEATURE:
<223> OTHER INFORMATION: synthetic construct

<400> SEQUENCE: 21
gccaaauacc ucuauaaaau uucuacuuuu guagau                36

<210> SEQ ID NO 22
<211> LENGTH: 32
<212> TYPE: RNA
<213> ORGANISM: Artificial Sequence
<220> FEATURE:
<223> OTHER INFORMATION: synthetic construct

<400> SEQUENCE: 22
guuucaaucc acgcgcccac gcggggcgcg ac                    32

<210> SEQ ID NO 23
<211> LENGTH: 35
<212> TYPE: RNA
<213> ORGANISM: Artificial Sequence
<220> FEATURE:
<223> OTHER INFORMATION: synthetic construct

<400> SEQUENCE: 23
gucaaaagac cuuuuuaauu ucuacucuug uagau                 35

<210> SEQ ID NO 24
<211> LENGTH: 36
<212> TYPE: RNA
<213> ORGANISM: Artificial Sequence
<220> FEATURE:
<223> OTHER INFORMATION: synthetic construct

<400> SEQUENCE: 24
gcuuagaaca uuuaaagaau uucuacuauu guagau                36

<210> SEQ ID NO 25
<211> LENGTH: 35

```
<212> TYPE: RNA
<213> ORGANISM: Artificial Sequence
<220> FEATURE:
<223> OTHER INFORMATION: synthetic construct

<400> SEQUENCE: 25
cucaaaacuc auucgaaucu cuacucuuug uagau                                      35

<210> SEQ ID NO 26
<211> LENGTH: 36
<212> TYPE: RNA
<213> ORGANISM: Artificial Sequence
<220> FEATURE:
<223> OTHER INFORMATION: synthetic construct

<400> SEQUENCE: 26
guuugaauaa ccuuaaauaa uuucuacuuu guagau                                     36

<210> SEQ ID NO 27
<211> LENGTH: 36
<212> TYPE: RNA
<213> ORGANISM: Artificial Sequence
<220> FEATURE:
<223> OTHER INFORMATION: synthetic construct

<400> SEQUENCE: 27
gucuaacgac cuuuuaaauu ucacuguuu guagau                                      36

<210> SEQ ID NO 28
<211> LENGTH: 36
<212> TYPE: RNA
<213> ORGANISM: Artificial Sequence
<220> FEATURE:
<223> OTHER INFORMATION: synthetic construct

<400> SEQUENCE: 28
cucuaaagag aggaaagaau uucuacuuuu guagau                                     36

<210> SEQ ID NO 29
<211> LENGTH: 36
<212> TYPE: RNA
<213> ORGANISM: Artificial Sequence
<220> FEATURE:
<223> OTHER INFORMATION: synthetic construct

<400> SEQUENCE: 29
guuucaaaga uuaaauaauu ucacuaagu guagau                                      36

<210> SEQ ID NO 30
<211> LENGTH: 36
<212> TYPE: RNA
<213> ORGANISM: Artificial Sequence
<220> FEATURE:
<223> OTHER INFORMATION: synthetic construct

<400> SEQUENCE: 30
gucuagguac ucucuuuaau uucuacuauu guagau                                     36

<210> SEQ ID NO 31
<211> LENGTH: 36
<212> TYPE: RNA
<213> ORGANISM: Artificial Sequence
<220> FEATURE:
<223> OTHER INFORMATION: synthetic construct

<400> SEQUENCE: 31
```
gucaauaaga cucauuuaau uucuacuucg guagau    36

<210> SEQ ID NO 32
<211> LENGTH: 36
<212> TYPE: RNA
<213> ORGANISM: Artificial Sequence
<220> FEATURE:
<223> OTHER INFORMATION: synthetic construct

<400> SEQUENCE: 32
gccuauaagg cuuuaguaau uucuacuauu guagau    36

<210> SEQ ID NO 33
<211> LENGTH: 1259
<212> TYPE: DNA
<213> ORGANISM: Artificial Sequence
<220> FEATURE:
<223> OTHER INFORMATION: synthetic construct

<400> SEQUENCE: 33
atgacacagt tcgagggctt taccaacctg tatcaggtga gcaagacact gcggtttgag    60
ctgatcccac agggcaagac cctgaagcac atccaggagc agggcttcat cgaggaggac   120
aaggcccgca atgatcacta caaggagctg aagcccatca tcgatcggat ctacaagacc   180
tatgccgacc agtgcctgca gctggtgcag ctggattggg agaacctgag cgccgccatc   240
gactcctata gaaaggagaa aaccgaggag acaaggaacg ccctgatcga ggagcaggcc   300
acatatcgca atgccatcca cgactacttc atcggccgga cagacaacct gaccgatgcc   360
atcaataaga gacacgccga gatctacaag ggcctgttca aggccgagct gtttaatggc   420
aaggtgctga gcagctggg caccgtgacc acaaccgagc acgagaacgc cctgctgcgg   480
agcttcgaca gtttacaac ctacttctcc ggcttttatg agaacaggaa gaacgtgttc   540
agcgccgagg atatcagcac agccatccca caccgcatcg tgcaggacaa cttccccaag   600
tttaaggaga attgtcacat cttcacacgc ctgatcaccg ccgtgcccag cctgcgggag   660
cactttgaga cgtgaagaa ggccatcggc atcttcgtga gcacctccat cgaggaggtg   720
ttttccttcc cttttataa ccagctgctg acacagaccc agatcgacct gtataaccag   780
ctgctgggag gaatctctcg ggaggcaggc accgagaaga tcaagggcct gaacgaggtg   840
ctgaatctgg ccatccagaa gaatgatgag acagcccaca tcatcgcctc cctgccacac   900
agattcatcc ccctgtttaa gcagatcctg tccgatagga cacccctgtc tttcatcctg   960
gaggagttta gagcgacga ggaagtgatc cagtccttct gcaagtacaa gacactgctg  1020
agaaacgaga acgtgctgga gacagccgag gccctgtta acgagctgaa cagcatcgac  1080
ctgacacaca tcttcatcag ccacaagaag ctggagacaa tcagcagcgc cctgtgcgac  1140
cactgggata cactgaggaa tgccctgtat gagcggagaa tctccgagct gacaggcaag  1200
atcaccaagt ctgccaagga gaaggtgcag cgcagcctga gcacgagga tatcaacct   1259

<210> SEQ ID NO 34
<211> LENGTH: 46
<212> TYPE: RNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)..(3)
<223> OTHER INFORMATION: modified with a 2'-Fluoro (2'-F) chemically
      modified ribose
<220> FEATURE:

```
<221> NAME/KEY: misc_feature
<222> LOCATION: (42)..(46)
<223> OTHER INFORMATION: modified with a 2'-Fluoro (2'-F) chemically
      modified ribose

<400> SEQUENCE: 34
ggguaauuuc uacucuugua gaucugaugg uccaugucug uuacuc            46

<210> SEQ ID NO 35
<211> LENGTH: 46
<212> TYPE: RNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)..(3)
<223> OTHER INFORMATION: 2'-O-methyl (2'-O-Me) chemically modified
      ribose and a phosphorothioate (PS) chemically modified
      phosphodiester linkage
<220> FEATURE:
<221> NAME/KEY: misc_feature
<222> LOCATION: (42)..(46)
<223> OTHER INFORMATION: modified with a 2'-Fluoro (2'-F) chemically
      modified ribose

<400> SEQUENCE: 35
ggguaauuuc uacucuugua gaucugaugg uccaugucug uuacuc            46

<210> SEQ ID NO 36
<211> LENGTH: 46
<212> TYPE: RNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)..(3)
<223> OTHER INFORMATION: modified with a 2'-Fluoro (2'-F) chemically
      modified ribose
<220> FEATURE:
<221> NAME/KEY: misc_feature
<222> LOCATION: (42)..(46)
<223> OTHER INFORMATION: modified with a 2'-Fluoro (2'-F) chemically
      modified ribose

<400> SEQUENCE: 36
uuuuaauuuc uacucuugua gaucugaugg uccaugucug uuacuc            46

<210> SEQ ID NO 37
<211> LENGTH: 46
<212> TYPE: RNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)..(3)
<223> OTHER INFORMATION: 2'-O-methyl (2'-O-Me) chemically modified
      ribose and a phosphorothioate (PS) chemically modified
      phosphodiester linkage
<220> FEATURE:
<221> NAME/KEY: misc_feature
<222> LOCATION: (42)..(46)
<223> OTHER INFORMATION: modified with a 2'-Fluoro (2'-F) chemically
      modified ribose

<400> SEQUENCE: 37
uuuuaauuuc uacucuugua gaucugaugg uccaugucug uuacuc            46

<210> SEQ ID NO 38
```

```
<211> LENGTH: 48
<212> TYPE: RNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)..(5)
<223> OTHER INFORMATION: modified with a 2'-Fluoro (2'-F) chemically
      modified ribose
<220> FEATURE:
<221> NAME/KEY: misc_feature
<222> LOCATION: (44)..(48)
<223> OTHER INFORMATION: modified with a 2'-Fluoro (2'-F) chemically
      modified ribose

<400> SEQUENCE: 38
cuuuuuaauu ucuacucuug uagaucugau gguccauguc uguuacuc                 48

<210> SEQ ID NO 39
<211> LENGTH: 48
<212> TYPE: RNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)..(5)
<223> OTHER INFORMATION: 2'-O-methyl (2'-O-Me) chemically modified
      ribose and a phosphorothioate (PS) chemically modified
      phosphodiester linkage
<220> FEATURE:
<221> NAME/KEY: misc_feature
<222> LOCATION: (44)..(48)
<223> OTHER INFORMATION: modified with a 2'-Fluoro (2'-F) chemically
      modified ribose

<400> SEQUENCE: 39
cuuuuuaauu ucuacucuug uagaucugau gguccauguc uguuacuc                 48

<210> SEQ ID NO 40
<211> LENGTH: 46
<212> TYPE: RNA
<213> ORGANISM: Artificial Sequence
<220> FEATURE:
<223> OTHER INFORMATION: synthetic construct

<400> SEQUENCE: 40
ggguaauuuc uacucuugua gauggaugug uucuuaccac agaggg                   46

<210> SEQ ID NO 41
<211> LENGTH: 43
<212> TYPE: RNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (39)..(43)
<223> OTHER INFORMATION: modified with a 2'-Fluoro (2'-F) chemically
      modified ribose

<400> SEQUENCE: 41
uaauuucuac ucuuguagau ggauguguuc uuaccacaga ggg                      43

<210> SEQ ID NO 42
<211> LENGTH: 51
<212> TYPE: RNA
<213> ORGANISM: Artificial Sequence
<220> FEATURE:
<223> OTHER INFORMATION: synthetic construct
```

-continued

```
<220> FEATURE:
<221> NAME/KEY: misc_feature
<222> LOCATION: (1)..(5)
<223> OTHER INFORMATION: modified with a 2'-Fluoro (2'-F) chemically
      modified ribose
<220> FEATURE:
<221> NAME/KEY: misc_feature
<222> LOCATION: (47)..(51)
<223> OTHER INFORMATION: modified with a 2'-Fluoro (2'-F) chemically
      modified ribose

<400> SEQUENCE: 42
cuuuugggua auuucuacuc uuguagaugg auguguucuu accacagagg g         51

<210> SEQ ID NO 43
<211> LENGTH: 43
<212> TYPE: RNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (5)..(6)
<223> OTHER INFORMATION: modified with a 2'-Fluoro (2'-F) chemically
      modified ribose
<220> FEATURE:
<221> NAME/KEY: misc_feature
<222> LOCATION: (9)..(10)
<223> OTHER INFORMATION: modified with a 2'-Fluoro (2'-F) chemically
      modified ribose
<220> FEATURE:
<221> NAME/KEY: misc_feature
<222> LOCATION: (12)..(14)
<223> OTHER INFORMATION: modified with a 2'-Fluoro (2'-F) chemically
      modified ribose
<220> FEATURE:
<221> NAME/KEY: misc_feature
<222> LOCATION: (16)..(19)
<223> OTHER INFORMATION: modified with a 2'-Fluoro (2'-F) chemically
      modified ribose
<220> FEATURE:
<221> NAME/KEY: misc_feature
<222> LOCATION: (29)..(32)
<223> OTHER INFORMATION: modified with a 2'-Fluoro (2'-F) chemically
      modified ribose
<220> FEATURE:
<221> NAME/KEY: misc_feature
<222> LOCATION: (37)..(37)
<223> OTHER INFORMATION: modified with a 2'-Fluoro (2'-F) chemically
      modified ribose
<220> FEATURE:
<221> NAME/KEY: misc_feature
<222> LOCATION: (39)..(43)
<223> OTHER INFORMATION: modified with a 2'-Fluoro (2'-F) chemically
      modified ribose

<400> SEQUENCE: 43
uaauuucuac ucuuguagau ggauguguuc uuaccacaga ggg                  43

<210> SEQ ID NO 44
<211> LENGTH: 46
<212> TYPE: RNA
<213> ORGANISM: Artificial Sequence
<220> FEATURE:
<223> OTHER INFORMATION: synthetic construct

<400> SEQUENCE: 44
ggguaauuuc uacucuugua gaucuuccac ccggauaaga ugcugg               46

<210> SEQ ID NO 45
<211> LENGTH: 48
<212> TYPE: RNA
<213> ORGANISM: Artificial Sequence
```

```
<220> FEATURE:
<223> OTHER INFORMATION: synthetic construct
<220> FEATURE:
<221> NAME/KEY: misc_feature
<222> LOCATION: (1)..(5)
<223> OTHER INFORMATION: modified with a 2'-Fluoro (2'-F) chemically
      modified ribose
<220> FEATURE:
<221> NAME/KEY: misc_feature
<222> LOCATION: (44)..(48)
<223> OTHER INFORMATION: modified with a 2'-Fluoro (2'-F) chemically
      modified ribose

<400> SEQUENCE: 45
cuuuuuaauu ucuacucuug uagaucuucc acccggauaa gaugcugg                 48

<210> SEQ ID NO 46
<211> LENGTH: 16
<212> TYPE: RNA
<213> ORGANISM: Artificial Sequence
<220> FEATURE:
<223> OTHER INFORMATION: synthetic construct

<400> SEQUENCE: 46
gucuagaaac uuuaaa                                                    16

<210> SEQ ID NO 47
<211> LENGTH: 15
<212> TYPE: RNA
<213> ORGANISM: Artificial Sequence
<220> FEATURE:
<223> OTHER INFORMATION: synthetic construct

<400> SEQUENCE: 47
guuuuggagu accuu                                                     15

<210> SEQ ID NO 48
<211> LENGTH: 14
<212> TYPE: RNA
<213> ORGANISM: Artificial Sequence
<220> FEATURE:
<223> OTHER INFORMATION: synthetic construct

<400> SEQUENCE: 48
guuuuagaac cuua                                                      14

<210> SEQ ID NO 49
<211> LENGTH: 16
<212> TYPE: RNA
<213> ORGANISM: Artificial Sequence
<220> FEATURE:
<223> OTHER INFORMATION: synthetic construct

<400> SEQUENCE: 49
guuuaaaagu ccuauu                                                    16

<210> SEQ ID NO 50
<211> LENGTH: 16
<212> TYPE: RNA
<213> ORGANISM: Artificial Sequence
<220> FEATURE:
<223> OTHER INFORMATION: synthetic construct

<400> SEQUENCE: 50
gccaaauacc ucuaua                                                    16

<210> SEQ ID NO 51
```

```
<211> LENGTH: 11
<212> TYPE: RNA
<213> ORGANISM: Artificial Sequence
<220> FEATURE:
<223> OTHER INFORMATION: synthetic construct

<400> SEQUENCE: 51
guuucaaucc a                                                              11

<210> SEQ ID NO 52
<211> LENGTH: 15
<212> TYPE: RNA
<213> ORGANISM: Artificial Sequence
<220> FEATURE:
<223> OTHER INFORMATION: synthetic construct

<400> SEQUENCE: 52
gucaaaagac cuuuu                                                          15

<210> SEQ ID NO 53
<211> LENGTH: 16
<212> TYPE: RNA
<213> ORGANISM: Artificial Sequence
<220> FEATURE:
<223> OTHER INFORMATION: synthetic construct

<400> SEQUENCE: 53
gcuuagaaca uuuaaa                                                         16

<210> SEQ ID NO 54
<211> LENGTH: 14
<212> TYPE: RNA
<213> ORGANISM: Artificial Sequence
<220> FEATURE:
<223> OTHER INFORMATION: synthetic construct

<400> SEQUENCE: 54
cucaaaacuc auuc                                                           14

<210> SEQ ID NO 55
<211> LENGTH: 17
<212> TYPE: RNA
<213> ORGANISM: Artificial Sequence
<220> FEATURE:
<223> OTHER INFORMATION: synthetic construct

<400> SEQUENCE: 55
guuugaauaa ccuuaaa                                                        17

<210> SEQ ID NO 56
<211> LENGTH: 15
<212> TYPE: RNA
<213> ORGANISM: Artificial Sequence
<220> FEATURE:
<223> OTHER INFORMATION: synthetic construct

<400> SEQUENCE: 56
gucuaacgac cuuuu                                                          15

<210> SEQ ID NO 57
<211> LENGTH: 16
<212> TYPE: RNA
<213> ORGANISM: Artificial Sequence
<220> FEATURE:
<223> OTHER INFORMATION: synthetic construct

<400> SEQUENCE: 57
```

```
cucuaaagag aggaaa                                                   16

<210> SEQ ID NO 58
<211> LENGTH: 15
<212> TYPE: RNA
<213> ORGANISM: Artificial Sequence
<220> FEATURE:
<223> OTHER INFORMATION: synthetic construct

<400> SEQUENCE: 58
guuucaaaga uuaaa                                                    15

<210> SEQ ID NO 59
<211> LENGTH: 16
<212> TYPE: RNA
<213> ORGANISM: Artificial Sequence
<220> FEATURE:
<223> OTHER INFORMATION: synthetic construct

<400> SEQUENCE: 59
gucuagguac ucucuu                                                   16

<210> SEQ ID NO 60
<211> LENGTH: 16
<212> TYPE: RNA
<213> ORGANISM: Artificial Sequence
<220> FEATURE:
<223> OTHER INFORMATION: synthetic construct

<400> SEQUENCE: 60
gucaauaaga cucauu                                                   16

<210> SEQ ID NO 61
<211> LENGTH: 16
<212> TYPE: RNA
<213> ORGANISM: Artificial Sequence
<220> FEATURE:
<223> OTHER INFORMATION: synthetic construct

<400> SEQUENCE: 61
gccuauaagg cuuuag                                                   16

<210> SEQ ID NO 62
<211> LENGTH: 20
<212> TYPE: RNA
<213> ORGANISM: Artificial Sequence
<220> FEATURE:
<223> OTHER INFORMATION: synthetic construct

<400> SEQUENCE: 62
uaauuucuac uguuguagau                                               20

<210> SEQ ID NO 63
<211> LENGTH: 21
<212> TYPE: RNA
<213> ORGANISM: Artificial Sequence
<220> FEATURE:
<223> OTHER INFORMATION: synthetic construct

<400> SEQUENCE: 63
agaaaugcau gguucucaug c                                             21

<210> SEQ ID NO 64
<211> LENGTH: 21
<212> TYPE: RNA
```

<213> ORGANISM: Artificial Sequence
<220> FEATURE:
<223> OTHER INFORMATION: synthetic construct

<400> SEQUENCE: 64
aaaauuaccu aguaauuagg u                                                    21

<210> SEQ ID NO 65
<211> LENGTH: 20
<212> TYPE: RNA
<213> ORGANISM: Artificial Sequence
<220> FEATURE:
<223> OTHER INFORMATION: synthetic construct

<400> SEQUENCE: 65
ggauuucuac uuuuguagau                                                      20

<210> SEQ ID NO 66
<211> LENGTH: 20
<212> TYPE: RNA
<213> ORGANISM: Artificial Sequence
<220> FEATURE:
<223> OTHER INFORMATION: synthetic construct

<400> SEQUENCE: 66
aaauuucuac uuuuguagau                                                      20

<210> SEQ ID NO 67
<211> LENGTH: 21
<212> TYPE: RNA
<213> ORGANISM: Artificial Sequence
<220> FEATURE:
<223> OTHER INFORMATION: synthetic construct

<400> SEQUENCE: 67
cgcgcccacg cggggcgcga c                                                    21

<210> SEQ ID NO 68
<211> LENGTH: 20
<212> TYPE: RNA
<213> ORGANISM: Artificial Sequence
<220> FEATURE:
<223> OTHER INFORMATION: synthetic construct

<400> SEQUENCE: 68
uaauuucuac ucuuguagau                                                      20

<210> SEQ ID NO 69
<211> LENGTH: 20
<212> TYPE: RNA
<213> ORGANISM: Artificial Sequence
<220> FEATURE:
<223> OTHER INFORMATION: synthetic construct

<400> SEQUENCE: 69
gaauuucuac uauuguagau                                                      20

<210> SEQ ID NO 70
<211> LENGTH: 21
<212> TYPE: RNA
<213> ORGANISM: Artificial Sequence
<220> FEATURE:
<223> OTHER INFORMATION: synthetic construct

<400> SEQUENCE: 70
gaaucucuac ucuuguaga u                                                     21

<210> SEQ ID NO 71
<211> LENGTH: 19
<212> TYPE: RNA
<213> ORGANISM: Artificial Sequence
<220> FEATURE:
<223> OTHER INFORMATION: synthetic construct

<400> SEQUENCE: 71
uaauuucuac uuuguagau                                                    19

<210> SEQ ID NO 72
<211> LENGTH: 21
<212> TYPE: RNA
<213> ORGANISM: Artificial Sequence
<220> FEATURE:
<223> OTHER INFORMATION: synthetic construct

<400> SEQUENCE: 72
aaauuucuac uguuuguaga u                                                 21

<210> SEQ ID NO 73
<211> LENGTH: 20
<212> TYPE: RNA
<213> ORGANISM: Artificial Sequence
<220> FEATURE:
<223> OTHER INFORMATION: synthetic construct

<400> SEQUENCE: 73
gaauuucuac uuuuguagau                                                   20

<210> SEQ ID NO 74
<211> LENGTH: 21
<212> TYPE: RNA
<213> ORGANISM: Artificial Sequence
<220> FEATURE:
<223> OTHER INFORMATION: synthetic construct

<400> SEQUENCE: 74
uaauuucuac uaaguguaga u                                                 21

<210> SEQ ID NO 75
<211> LENGTH: 20
<212> TYPE: RNA
<213> ORGANISM: Artificial Sequence
<220> FEATURE:
<223> OTHER INFORMATION: synthetic construct

<400> SEQUENCE: 75
uaauuucuac uauuguagau                                                   20

<210> SEQ ID NO 76
<211> LENGTH: 20
<212> TYPE: RNA
<213> ORGANISM: Artificial Sequence
<220> FEATURE:
<223> OTHER INFORMATION: synthetic construct

<400> SEQUENCE: 76
uaauuucuac uucgguagau                                                   20

<210> SEQ ID NO 77
<211> LENGTH: 20
<212> TYPE: RNA
<213> ORGANISM: Artificial Sequence
<220> FEATURE:

```
<223> OTHER INFORMATION: synthetic construct

<400> SEQUENCE: 77
uaauuucuac uauuguagau                                            20

<210> SEQ ID NO 78
<211> LENGTH: 18
<212> TYPE: RNA
<213> ORGANISM: Artificial Sequence
<220> FEATURE:
<223> OTHER INFORMATION: synthetic construct

<400> SEQUENCE: 78
cugauggucc augucugu                                              18

<210> SEQ ID NO 79
<211> LENGTH: 18
<212> TYPE: RNA
<213> ORGANISM: Artificial Sequence
<220> FEATURE:
<223> OTHER INFORMATION: synthetic construct

<400> SEQUENCE: 79
ggauguguuc uuaccaca                                              18

<210> SEQ ID NO 80
<211> LENGTH: 18
<212> TYPE: RNA
<213> ORGANISM: Artificial Sequence
<220> FEATURE:
<223> OTHER INFORMATION: synthetic construct

<400> SEQUENCE: 80
cuuccacccg gauaagau                                              18
```

ENGINEERED GUIDE RNA AND USES THEREOF

CROSS REFERENCE TO RELATED APPLICATIONS

This application claims the benefit of U.S. Provisional Patent Application Ser. No. 62/626,827 filed Feb. 6, 2018, the disclosure of which is expressly incorporated herein by reference.

STATEMENT OF GOVERNMENT SUPPORT

This invention was made with government support under grant GM119679 awarded by the National Institutes of Health. The government has certain rights in this invention.

REFERENCE TO SEQUENCE LISTING

The Sequence Listing submitted Feb. 6, 2019, as a text file named "10336-292US1 2019_02_06 ST25.txt," created on Feb. 6, 2019, and having a size of 25,163 bytes is hereby incorporated by reference pursuant to 37 C.F.R. § 1.52 (e) (5).

FIELD OF THE INVENTION

The present disclosure generally relates to systems, methods and compositions for use in Clustered Regularly Interspaced Short Palindromic Repeats (CRISPR)-Cpf1 genome editing systems.

BACKGROUND

The bacterial type II CRISPR-Cas9 genome editing method has recently received a great deal of interest in the field of genome engineering. The co-expression of a single Cas9 protein isolated from *Streptococcus pyogenes* with a chimeric single guide RNA (sgRNA) can precisely create double stranded breaks (DSBs) in a genome. The Cas9 protein is directed to a precise DNA sequence in the genome by a twenty nucleotide target sequence present in the sgRNA, which guides the Cas9 protein to create the DSB. The presence of a double-stranded break in genomic DNA dramatically increases the rate of homologous recombination.

Recently, an additional genome editing system, termed the CRISPR-Cpf1 system, was identified (Zetsche, B. et al. Cpf1 is a single RNA-guided endonuclease of a class 2 CRISPR-Cas system. Cell. 2015 Oct. 22; 163 (3): 759-71). Cpf1 cleaves DNA in a staggered pattern and leaves sticky ends, as compared to the cleaved blunt DNA ends left by the Cas9 enzyme. In addition, Cpf1 only requires one guide RNA rather than the two (tracrRNA and crRNA) needed by Cas9 for cleavage (or a chimeric single guide RNA). However, gene editing frequencies are still very low, and thus new methods are needed to modify the guide RNA sequences in order to improve the efficiency of the CRISPR-Cpf1 gene editing system.

The systems, methods, and compositions disclosed herein address these and other needs.

SUMMARY

Disclosed herein are systems, methods, and compositions that utilize engineered guide RNAs (gRNA or crRNA) in the CRISPR-Cpf1 genome editing system. These modified RNAs comprise extensions at the 5' and/or 3' ends of the guide RNA. In addition, these guide RNAs can incorporate a number of chemical changes to the nucleotides, including changes to the nucleobase, the ribose sugar, and/or the phosphodiester linkage.

In some aspects, disclosed herein is a genome editing system comprising:
  a) a guide RNA comprising a guide segment that hybridizes with a target sequence of a DNA molecule in a eukaryotic cell to form an RNA/DNA hybrid, and wherein the guide RNA forms a stem loop 5' of the RNA/DNA hybrid, and
  b) an mRNA encoding a Cpf1 protein;
  wherein the guide RNA comprises from 1 to 50 additional nucleotides 5' of the stem loop.

In other aspects, disclosed herein is a method of RNA-guided genome editing, the method comprising:
  introducing into a cell of the subject:
  a) a guide RNA comprising a guide segment that hybridizes with a target sequence of a DNA molecule in a eukaryotic cell to form an RNA/DNA hybrid, and wherein the guide RNA forms a stem loop 5' of the RNA/DNA hybrid, and
  b) an mRNA encoding a Cpf1 protein;
  wherein the guide RNA comprises from 1 to 50 additional nucleotides 5' of the stem loop; and
  wherein the guide RNA hybridizes with the target sequence and the Cpf1 protein cleaves the DNA molecule.

In some aspects, disclosed herein is a genome editing system comprising:
  a) a guide RNA comprising a guide segment that hybridizes with a target sequence of a DNA molecule in a eukaryotic cell to form an RNA/DNA hybrid, and wherein the guide RNA forms a stem loop 5' of the RNA/DNA hybrid, and
  b) an mRNA encoding a Cpf1 protein;
  wherein the guide RNA comprises from 1 to 50 additional nucleotides 5' of the stem loop; and
  wherein the guide RNA comprises from 1 to 50 additional nucleotides 3' of the guide segment.

In other aspects, disclosed herein is a method of RNA-guided genome editing, the method comprising:
  introducing into a cell of the subject:
  a) a guide RNA comprising a guide segment that hybridizes with a target sequence of a DNA molecule in a eukaryotic cell to form an RNA/DNA hybrid, and wherein the guide RNA forms a stem loop 5' of the RNA/DNA hybrid, and
  b) an mRNA encoding a Cpf1 protein;
  wherein the guide RNA comprises from 1 to 50 additional nucleotides 5' of the stem loop;
  wherein the guide RNA comprises from 1 to 50 additional nucleotides 3' of the guide segment;
  and wherein the guide RNA hybridizes with the target sequence and the Cpf1 protein cleaves the DNA molecule.

In some embodiments, the guide RNA comprises a sequence selected from SEQ ID NO:1, SEQ ID NO:2, SEQ ID NO:3, SEQ ID NO:4, SEQ ID NO:5, SEQ ID NO:6, SEQ ID NO:7, SEQ ID NO: 8, SEQ ID NO:9, SEQ ID NO: 10, SEQ ID NO:11, SEQ ID NO:12, SEQ ID NO:13, SEQ ID NO: 14, SEQ ID NO:15, SEQ ID NO:16, SEQ ID NO:34, SEQ ID NO:35, SEQ ID NO:36, SEQ ID NO:37, SEQ ID NO:38, or SEQ ID NO:39.

In some embodiments, the guide RNA comprises from 10 to 40 nucleotides 5' of the stem loop. In some embodiments, the guide RNA comprises from 20 to 30 nucleotides 5' of the stem loop.

In some embodiments, the guide RNA comprises from 1 to 50 additional nucleotides 3' (downstream) of a guide segment.

In some embodiments, the additional nucleotides 5' of the stem loop are heterologous nucleotides. In some embodiments, the heterologous nucleotides comprise a second RNA sequence from a different species compared to the guide segment, the stem loop, and/or the RNA/DNA hybrid.

In some embodiments, the guide RNA comprises at least one chemically modified nucleotide. In some embodiments, the at least one chemically modified nucleotide comprises a chemically modified nucleobase, a chemically modified ribose, a chemically modified phosphodiester linkage, or a combination thereof.

BRIEF DESCRIPTION OF THE DRAWINGS

The accompanying figures, which are incorporated in and constitute a part of this specification, illustrate several aspects described below.

FIG. 3A. A schematic showing examples of chemical changes to the chemically modified nucleotides utilized for guide RNAs or Cpf1 mRNAs. FIG. 3B. A panel showing examples of chemically modified phosphodiester linkages for the chemically modified nucleotides utilized for guide RNAs or Cpf1 mRNAs. Boxed phosphodiester linkage shows the natural unit. FIG. 3C. A panel showing examples of chemically modified ribose sugar moieties for the chemically modified nucleotides utilized for guide RNAs or Cpf1 mRNAs. Boxed ribose shows the natural unit.

FIG. 3D. A panel showing examples of chemically modified nucleobases for the chemically modified nucleotides utilized for guide RNAs or Cpf1 mRNAs.

IVT crRNA5:
(SEQ ID NO: 40)
5'-GGGUAAUUUCUACUCUUGUAGAUGGAUGUGUUCUUACCACAGAGG

G-3' crRNA5 1F:
(SEQ ID NO: 41)
5'-UAAUUUCUACUCUUGUAGAUGGAUGUGUUCUUACCAC<u>AGAGGG</u>-3' crRNA5 2F:
(SEQ ID NO: 42)
5'-<u>CUUUU</u>GGGUAAUUUCUACUCUUGUAGAUGGAUGUGUUCUUACCAC<u>AG</u>

<u>AGGG</u>-3' crRNA5 21F:
(SEQ ID NO: 43)
5'-UAA<u>U</u>UUC<u>U</u>AC<u>U</u>C<u>U</u>UGUAGAUGGAUGUGU<u>U</u>C<u>U</u>UACC<u>AC</u>AG<u>AGGG</u>-3'

Figure 6:
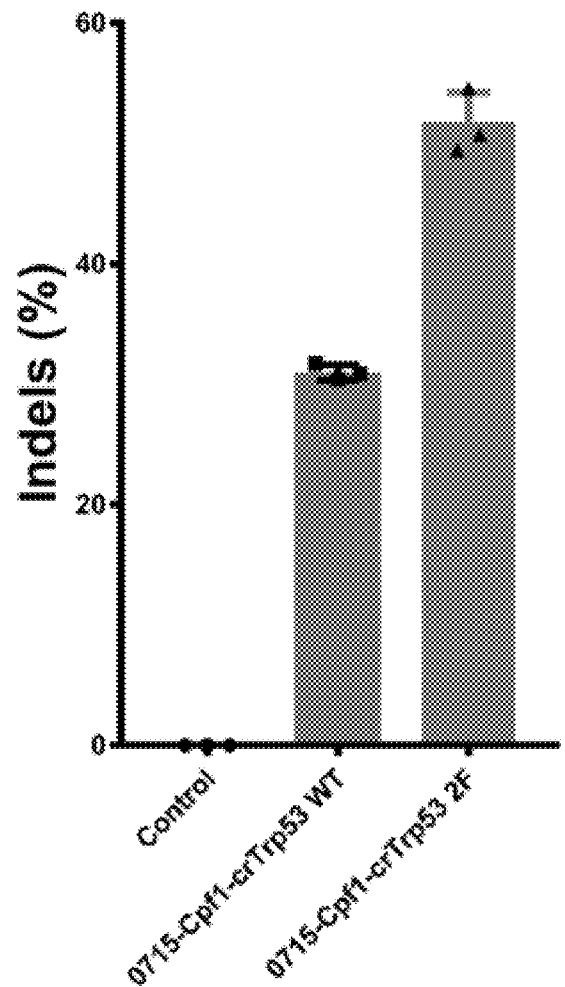

FIG. 6. Modified guide RNA (crTrp53 2F) significantly improved gene editing efficiency compared to the wild type guide RNA, IVT crTrp53 in the stem cells. Sequences (Underlined sequences represent nucleotides with a modified with a 2'-Fluoro (2' F) chemically modified ribose):

IVT crTrp53:
(SEQ ID NO: 44)
5'-GGGUAAUUUCUACUCUUGUAGAUCUUCCACCCGGAUAAGAUGCUG

G-3' crTrp532F:
(SEQ ID NO: 45)
5'-<u>CUUUU</u>UAAUUUCUACUCUUGUAGAUCUUCCACCCGGAUAAGAUGC

<u>U</u>GG-3'

DETAILED DESCRIPTION OF THE INVENTION

Disclosed herein are systems, methods, and compositions that utilize engineered guide RNAs (gRNA or crRNA) in the CRISPR-Cpf1 genome editing system. These modified RNAs comprise extensions at the 5' and/or 3' ends of the guide RNA. In addition, these guide RNAs can incorporate a number of chemical changes to the nucleotides, including changes to the nucleobase, the ribose sugar, and/or the phosphodiester linkage.

Reference will now be made in detail to the embodiments of the invention, examples of which are illustrated in the drawings and the examples. This invention may, however, be embodied in many different forms and should not be construed as limited to the embodiments set forth herein.

Unless defined otherwise, all technical and scientific terms used herein have the same meaning as commonly understood to one of ordinary skill in the art to which this invention belongs. The following definitions are provided for the full understanding of terms used in this specification.

Terminology

As used herein, the article "a," "an," and "the" means "at least one," unless the context in which the article is used clearly indicates otherwise.

The term "nucleic acid" as used herein means a polymer composed of nucleotides, e.g. deoxyribonucleotides or ribonucleotides.

The terms "ribonucleic acid" and "RNA" as used herein mean a polymer composed of ribonucleotides.

The terms "deoxyribonucleic acid" and "DNA" as used herein mean a polymer composed of deoxyribonucleotides.

The term "oligonucleotide" denotes single- or double-stranded nucleotide multimers of from about 2 to up to about 100 nucleotides in length. Suitable oligonucleotides may be prepared by the phosphoramidite method described by Beaucage and Carruthers, Tetrahedron Lett., 22:1859-1862 (1981), or by the triester method according to Matteucci, et al., J. Am. Chem. Soc., 103:3185 (1981), both incorporated herein by reference, or by other chemical methods using either, commercial automated oligonucleotide synthesizer or VLSIPS™ technology. When oligonucleotides are referred to as "double-stranded," it is understood by those of skill in the art that a pair of oligonucleotides exist in a hydrogen-bonded, helical array typically associated with, for example, DNA. In addition to the 100% complementary form of double-stranded oligonucleotides, the term "double-stranded," as used herein is also meant to refer to those forms which include such structural features as bulges and loops, described more fully in such biochemistry texts as Stryer, Biochemistry, Third Ed., (1988), incorporated herein by reference for all purposes.

The term "polynucleotide" refers to a single or double stranded polymer composed of nucleotide monomers. In some embodiments, the polynucleotide is composed of nucleotide monomers of generally greater than 100 nucleotides in length and up to about 8,000 or more nucleotides in length (but can be any appropriate length).

The term "polypeptide" refers to a compound made up of a single chain of D- or L-amino acids or a mixture of D- and L-amino acids joined by peptide bonds.

The term "complementary" refers to the topological compatibility or matching together of interacting surfaces of a probe molecule and its target. Thus, the target and its probe can be described as complementary, and furthermore, the contact surface characteristics are complementary to each other.

The term "hybridization" refers to a process of establishing a non-covalent, sequence-specific interaction between two or more complementary strands of nucleic acids into a single hybrid, which in the case of two strands is referred to as a duplex.

The term "anneal" refers to the process by which a single-stranded nucleic acid sequence pairs by hydrogen bonds to a complementary sequence, forming a double-stranded nucleic acid sequence, including the reformation (renaturation) of complementary strands that were separated by heat (thermally denatured).

The term "melting" refers to the denaturation of a double-stranded nucleic acid sequence due to high temperatures, resulting in the separation of the double strand into two single strands by breaking the hydrogen bonds between the strands.

The term "target" refers to a molecule that has an affinity for a given probe. Targets may be naturally-occurring or man-made molecules. Also, they can be employed in their unaltered state or as aggregates with other species.

The term "promoter" or "regulatory element" refers to a region or sequence determinants located upstream or downstream from the start of transcription and which are involved in recognition and binding of RNA polymerase and other proteins to initiate transcription. Promoters need not be of bacterial origin, for example, promoters derived from viruses or from other organisms can be used in the compositions, systems, or methods described herein. The term "regulatory element" is intended to include promoters, enhancers, internal ribosomal entry sites (IRES), and other expression control elements (e.g. transcription termination signals, such as polyadenylation signals and poly-U sequences). Such regulatory elements are described, for example, in Goeddel, Gene Expression Technology: Methods in Enzymology 185, Academic Press, San Diego, Calif. (1990). Regulatory elements include those that direct constitutive expression of a nucleotide sequence in many types of host cell and those that direct expression of the nucleotide sequence only in certain host cells (e.g., tissue-specific regulatory sequences). A tissue-specific promoter may direct expression primarily in a desired tissue of interest, such as muscle, neuron, bone, skin, blood, specific organs (e.g. liver, pancreas), or particular cell types (e.g. lymphocytes). Regulatory elements may also direct expression in a temporal-dependent manner, such as in a cell-cycle dependent or developmental stage-dependent manner, which may or may not also be tissue or cell-type specific. In some embodiments, a vector comprises one or more pol III promoter (e.g. 1, 2, 3, 4, 5, or more pol I promoters), one or more pol II promoters (e.g. 1, 2, 3, 4, 5, or more pol II promoters), one or more pol I promoters (e.g. 1, 2, 3, 4, 5, or more pol I promoters), or combinations thereof. Examples of pol III promoters include, but are not limited to, U6 and H1 promoters. Examples of pol II promoters include, but are not limited to, the retroviral Rous sarcoma virus (RSV) LTR promoter (optionally with the RSV enhancer), the cytomegalovirus (CMV) promoter (optionally with the CMV enhancer) [see, e.g., Boshart et al, Cell, 41:521-530 (1985)], the SV40 promoter, the dihydrofolate reductase promoter, the β-actin promoter, the phosphoglycerol kinase (PGK) promoter, and the EF1 a promoter. Also encompassed by the term "regulatory element" are enhancer elements, such as WPRE; CMV enhancers; the R-U5' segment in LTR of HTLV-I (Mol. Cell. Biol., Vol. 8 (1), p. 466-472, 1988); SV40 enhancer; and the intron sequence between exons 2 and 3 of rabbit β-globin (Proc. Natl. Acad. Sci. USA., Vol. 78 (3), p. 1527-31, 1981). It will be appreciated by those skilled in the art that the design of the expression vector can depend on such factors as the choice of the host cell to be transformed, the level of expression desired, etc.

The term "recombinant" refers to a human manipulated nucleic acid (e.g. polynucleotide) or a copy or complement of a human manipulated nucleic acid (e.g. polynucleotide), or if in reference to a protein (i.e, a "recombinant protein"), a protein encoded by a recombinant nucleic acid (e.g. polynucleotide). In embodiments, a recombinant expression cassette comprising a promoter operably linked to a second nucleic acid (e.g. polynucleotide) may include a promoter that is heterologous to the second nucleic acid (e.g. polynucleotide) as the result of human manipulation (e.g., by methods described in Sambrook et al., Molecular Cloning-A Laboratory Manual, Cold Spring Harbor Laboratory, Cold Spring Harbor, N.Y., (1989) or Current Protocols in Molecular Biology Volumes 1-3, John Wiley & Sons, Inc. (1994-1998)). In another example, a recombinant expression cassette may comprise nucleic acids (e.g. polynucleotides) combined in such a way that the nucleic acids (e.g. polynucleotides) are extremely unlikely to be found in nature. For instance, human manipulated restriction sites or plasmid vector sequences may flank or separate the promoter from the second nucleic acid (e.g. polynucleotide). One of skill will recognize that nucleic acids (e.g. polynucleotides) can be manipulated in many ways and are not limited to the examples above.

The term "expression cassette" refers to a nucleic acid construct, which when introduced into a host cell, results in transcription and/or translation of a RNA or polypeptide, respectively. In embodiments, an expression cassette comprising a promoter operably linked to a second nucleic acid (e.g. polynucleotide) may include a promoter that is heterologous to the second nucleic acid (e.g. polynucleotide) as the result of human manipulation (e.g., by methods described in Sambrook et al., Molecular Cloning-A Laboratory Manual, Cold Spring Harbor Laboratory, Cold Spring Harbor, N.Y., (1989) or Current Protocols in Molecular Biology Volumes 1-3, John Wiley & Sons, Inc. (1994-1998)). In some embodiments, an expression cassette comprising a terminator (or termination sequence) operably linked to a second nucleic acid (e.g. polynucleotide) may include a terminator that is heterologous to the second nucleic acid (e.g. polynucleotide) as the result of human manipulation. In some embodiments, the expression cassette comprises a promoter operably linked to a second nucleic acid (e.g. polynucleotide) and a terminator operably linked to the second nucleic acid (e.g. polynucleotide) as the result of human manipulation. In some embodiments, the expression cassette comprises an endogenous promoter. In some embodiments, the expression cassette comprises an endogenous terminator. In some embodiments, the expression cassette comprises a synthetic (or non-natural) promoter. In some embodiments, the expression cassette comprises a synthetic (or non-natural) terminator.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or higher identity over a specified region when compared and aligned for maximum correspondence over a comparison window or designated region) as measured using a BLAST or BLAST 2.0 sequence comparison algorithms with default parameters described below, or by manual alignment and visual inspection (see, e.g., NCBI web site or the like). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 10 amino acids or 20 nucleotides in length, or more preferably over a region that is 10-50 amino acids or 20-50 nucleotides in length. As used herein, percent (%) amino acid sequence identity is defined as the percentage of amino acids in a candidate sequence that are identical to the amino acids in a reference sequence, after aligning the sequences and introducing gaps, if necessary, to achieve the maximum percent sequence identity. Alignment for purposes of determining percent sequence identity can be achieved in various ways that are within the skill in the art, for instance, using publicly available computer software such as BLAST, BLAST-2, ALIGN, ALIGN-2 or Megalign (DNASTAR) software. Appropriate parameters for measuring alignment, including any algorithms needed to achieve maximal alignment over the full-length of the sequences being compared can be determined by known methods.

For sequence comparisons, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

One example of an algorithm that is suitable for determining percent sequence identity and sequence similarity are the BLAST and BLAST 2.0 algorithms, which are described in Altschul et al. (1977) *Nuc. Acids Res.* 25:3389-3402, and Altschul et al. (1990) *J. Mol. Biol.* 215:403-410, respectively. Software for performing BLAST analyses is publicly available through the National Center for Biotechnology Information (ncbi.nlm.nih.gov). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al. (1990) J. Mol. Biol. 215:403-410). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff (1989) *Proc. Natl. Acad.* Sci. USA 89:10915) alignments (B) of 50, expectation (E) of 10, M=5, N=−4, and a comparison of both strands.

The BLAST algorithm also performs a statistical analysis of the similarity between two sequences (see, e.g., Karlin and Altschul (1993) *Proc. Natl. Acad. Sci.* USA 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01.

The phrase "codon optimized" as it refers to genes or coding regions of nucleic acid molecules for the transformation of various hosts, refers to the alteration of codons in the gene or coding regions of polynucleic acid molecules to reflect the typical codon usage of a selected organism without altering the polypeptide encoded by the DNA. Such optimization includes replacing at least one, or more than one, or a significant number, of codons with one or more codons that are more frequently used in the genes of that selected organism.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are near each other, and, in the case of a secretory leader, contiguous and in reading phase. However, operably linked nucleic acids (e.g. enhancers and coding sequences) do not have to be contiguous. Linking is accomplished by ligation at convenient restriction sites. If such sites do not exist, the synthetic oligonucleotide adaptors or linkers are used in accordance with conventional practice. In embodiments, a promoter is operably linked with a coding sequence when it is capable of affecting (e.g. modulating relative to the absence of the promoter) the expression of a protein from that coding sequence (i.e., the coding sequence is under the transcriptional control of the promoter).

The term "nucleobase" refers to the part of a nucleotide that bears the Watson/Crick base-pairing functionality. The most common naturally-occurring nucleobases, adenine (A), guanine (G), uracil (U), cytosine (C), and thymine (T) bear the hydrogen-bonding functionality that binds one nucleic acid strand to another in a sequence specific manner.

As used throughout, by a "subject" (or a "host") is meant an individual. Thus, the "subject" can include, for example, domesticated animals, such as cats, dogs, etc., livestock (e.g., cattle, horses, pigs, sheep, goats, etc.), laboratory animals (e.g., mouse, rabbit, rat, guinea pig, etc.) mammals, non-human mammals, primates, non-human primates, rodents, birds, reptiles, amphibians, fish, and any other animal. The subject can be a mammal such as a primate or a human.

The terms "guide RNA", "gRNA", "CRISPR RNA", or "crRNA" are used interchangeably throughout the specification. This crRNA (or guide RNA) consists of a 5'-handle and a guide segment. Cpf1 protein interacts with the pseudoknot structure formed by the 5'-handle of crRNA (or guide RNA). The guide segment possesses complementary binding with the target DNA sequences.

A nucleotide sequence is "heterologous" to a second nucleotide sequence if it originates from a foreign species, or, if from the same species, is modified by human action from its original form. For example, a promoter operably linked to a heterologous coding sequence refers to a coding sequence from a species different from that from which the promoter was derived, or, if from the same species, a coding sequence which is different from naturally occurring allelic variants.

Genome Editing Systems

In some aspects, disclosed herein is a genome editing system comprising:
  a) a guide RNA comprising a guide segment that hybridizes with a target sequence of a DNA molecule in a eukaryotic cell to form an RNA/DNA hybrid, and wherein the guide RNA forms a stem loop 5' of the RNA/DNA hybrid, and
  b) an mRNA encoding a Cpf1 protein;
  wherein the guide RNA comprises from 1 to 50 additional nucleotides 5' of the stem loop.

In some aspects, disclosed herein is a genome editing system comprising:
  a) a guide RNA comprising a guide segment that hybridizes with a target sequence of a DNA molecule in a eukaryotic cell to form an RNA/DNA hybrid, and wherein the guide RNA forms a stem loop 5' of the RNA/DNA hybrid, and
  b) an mRNA encoding a Cpf1 protein;
  wherein the guide RNA comprises from 1 to 50 additional nucleotides 5' of the stem loop; and
  wherein the guide RNA comprises from 1 to 50 additional nucleotides 3' of the guide segment.

In some embodiments, the guide RNA comprises a sequence selected from SEQ ID NO:1, SEQ ID NO:2, SEQ ID NO:3, SEQ ID NO:4, SEQ ID NO:5, SEQ ID NO:6, SEQ ID NO:7, SEQ ID NO: 8, SEQ ID NO:9, SEQ ID NO:10, SEQ ID NO:11, SEQ ID NO: 12, SEQ ID NO:13, SEQ ID NO: 14, SEQ ID NO:15, or SEQ ID NO:16.

In some embodiments, the guide RNA comprises a sequence selected from SEQ ID NO:17, SEQ ID NO:18, SEQ ID NO: 19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, or SEQ ID NO:32.

In some embodiments, the guide RNA comprises a sequence selected from SEQ ID NO:34, SEQ ID NO:35, SEQ ID NO:36, SEQ ID NO:37, SEQ ID NO:38, or SEQ ID NO:39.

In some embodiments, the guide RNA comprises a sequence selected from SEQ ID NO:40, SEQ ID NO:41, SEQ ID NO:42, SEQ ID NO:43, SEQ ID NO:44, or SEQ ID NO:45.

In some embodiments, the guide RNA comprises a 5' extension sequence and a stem loop sequence. In some embodiments, the guide RNA comprises a 5' extension sequence. In some embodiments, the guide RNA comprises a 5' extension sequence selected from Table 2. In some embodiments, the guide RNA comprises a 5' extension sequence selected from SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, or SEQ ID NO:61.

In some embodiments, the guide RNA comprises a stem loop sequence. In some embodiments, the guide RNA comprises a stem loop sequence selected from Table 2. In some embodiments, the guide RNA comprises a stem loop sequence selected from SEQ ID NO:62, SEQ ID NO: 63, SEQ ID NO:64, SEQ ID NO:65, SEQ ID NO:66, SEQ ID NO:67, SEQ ID NO:68, SEQ ID NO:69, SEQ ID NO: 70, SEQ ID NO:71, SEQ ID NO: 72, SEQ ID NO: 73, SEQ ID NO:74, SEQ ID NO:75, SEQ ID NO:76, or SEQ ID NO:77.

In some embodiments, the guide RNA comprises a 5' extension sequence selected from SEQ ID NO:46 to SEQ ID NO:61 and a stem loop sequence selected from SEQ ID NO:62 to SEQ ID NO: 77. Thus, the various 5' extension sequences from various species can be combined with any of the stem loop sequences from any of the species listed in Tables 1, 2, and 3. In addition, these guide RNA sequences may have additional 5' extensions and 3' extensions. In some embodiments, the guide RNA comprises at least one chemically modified nucleotide. In some embodiments, the at least one chemically modified nucleotide comprises a chemically modified nucleobase, a chemically modified ribose, a chemically modified phosphodiester linkage, or a combination thereof.

In some embodiments, the guide RNA comprises a nucleic acid which is at least 60%, at least 75%, at least 80%, at least 85%, at least 90%, at least 95%, at least 97.5%, or at least 99% identical to SEQ ID NO:1, SEQ ID NO:2, SEQ ID NO:3, SEQ ID NO:4, SEQ ID NO:5, SEQ ID NO: 6, SEQ ID NO:7, SEQ ID NO:8, SEQ ID NO:9, SEQ ID NO:10, SEQ ID NO: 11, SEQ ID NO: 12, SEQ ID NO:13, SEQ ID NO:14, SEQ ID NO:15, or SEQ ID NO:16.

In some embodiments, the guide RNA comprises a nucleic acid which is at least 60%, at least 75%, at least 80%, at least 85%, at least 90%, at least 95%, at least 97.5%, or at least 99% identical to SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, or SEQ ID NO:32.

In some embodiments, the guide RNA comprises a nucleic acid which is at least 60%, at least 75%, at least 80%, at least 85%, at least 90%, at least 95%, at least 97.5%, or at least 99% identical to SEQ ID NO:34, SEQ ID NO:35, SEQ ID NO:36, SEQ ID NO:37, SEQ ID NO:38, or SEQ ID NO:39.

In some embodiments, the guide RNA comprises a nucleic acid which is at least 60%, at least 75%, at least 80%, at least 85%, at least 90%, at least 95%, at least 97.5%, or at least 99% identical to SEQ ID NO:40, SEQ ID NO:41, SEQ ID NO:42, SEQ ID NO:43, SEQ ID NO:44, or SEQ ID NO:45.

In some embodiments, the guide RNA comprises a nucleic acid which is at least 60%, at least 75%, at least 80%, at least 85%, at least 90%, at least 95%, at least 97.5%, or at least 99% identical to SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, or SEQ ID NO:61.

In some embodiments, the guide RNA comprises a nucleic acid which is at least 60%, at least 75%, at least 80%, at least 85%, at least 90%, at least 95%, at least 97.5%, or at least 99% identical to SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO: 70, SEQ ID NO:71, SEQ ID NO:72, SEQ ID NO:73, SEQ ID NO:74, SEQ ID NO:75, SEQ ID NO:76, or SEQ ID NO:77.

In some embodiments, the guide RNA comprises a 5' extension sequence selected from SEQ ID NO:46 to SEQ ID NO:61 and a stem loop sequence selected from SEQ ID NO:62 to SEQ ID NO: 77. Thus, the various 5' extension sequences from various species can be combined with any of the stem loop sequences from any of the species listed in Tables 1, 2, and 3. In addition, these guide RNA sequences may have additional 5' extensions and 3' extensions. In some embodiments, the guide RNA comprises at least one chemically modified nucleotide. In some embodiments, the at least one chemically modified nucleotide comprises a chemically modified nucleobase, a chemically modified ribose, a chemically modified phosphodiester linkage, or a combination thereof.

In some embodiments, the guide RNA further comprises from 10 to 40 nucleotides 5' of the stem loop. In some embodiments, the guide RNA further comprises from 20 to 30 nucleotides 5' of the stem loop.

In some embodiments, the guide RNA comprises from 1 to 50 additional nucleotides 3' (downstream) of a guide segment.

In some embodiments, the additional nucleotides 5' of the stem loop are heterologous nucleotides. In some embodiments, the additional nucleotides 3' of the guide segment are heterologous nucleotides. In some embodiments, the heterologous nucleotides comprise a second RNA sequence from a different species compared to the guide segment, the stem loop, and/or the RNA/DNA hybrid.

In some embodiments, the guide RNA hybridizes with the target sequence and the Cpf1 protein cleaves the DNA molecule.

In some embodiments, disclosed herein is a genome editing system comprising:
  a) a guide RNA comprising a guide segment that hybridizes with a target sequence of a DNA molecule in a eukaryotic cell to form an RNA/DNA hybrid, and wherein the guide RNA forms a stem loop 5' of the RNA/DNA hybrid, and
  b) an mRNA encoding a Cpf1 protein;
  wherein the guide RNA comprises from 1 to 50 additional nucleotides 5' of the stem loop;
  wherein the guide RNA comprises at least one chemically modified nucleotide; and
  wherein the mRNA encoding a Cpf1 protein comprises at least one chemically modified nucleotide.

In some embodiments, disclosed herein is a genome editing system comprising:
  a) a guide RNA comprising a guide segment that hybridizes with a target sequence of a DNA molecule in a eukaryotic cell to form an RNA/DNA hybrid, and wherein the guide RNA forms a stem loop 5' of the RNA/DNA hybrid, and
  b) a DNA vector comprising a regulatory element operable in a eukaryotic cell operably linked to a nucleotide sequence encoding a Cpf1 protein; an mRNA encoding a Cpf1 protein; or a Cpf1 protein;
  wherein the guide RNA comprises from 1 to 50 additional nucleotides 5' of the stem loop; and
  wherein the guide RNA comprises at least one chemically modified nucleotide.

In some aspects, disclosed herein is a genome editing system comprising:
  a) a guide RNA comprising a guide segment that hybridizes with a target sequence of a DNA molecule in a eukaryotic cell to form an RNA/DNA hybrid, and wherein the guide RNA forms a stem loop 5' of the RNA/DNA hybrid, and
  b) a DNA vector comprising a regulatory element operable in a eukaryotic cell operably linked to a nucleotide sequence encoding a Cpf1 protein;
  wherein the guide RNA comprises from 1 to 50 additional nucleotides 5' of the stem loop.

In some aspects, disclosed herein is a genome editing system comprising:
  a) a guide RNA comprising a guide segment that hybridizes with a target sequence of a DNA molecule in a eukaryotic cell to form an RNA/DNA hybrid, and wherein the guide RNA forms a stem loop 5' of the RNA/DNA hybrid, and
  b) a DNA vector comprising a regulatory element operable in a eukaryotic cell operably linked to a nucleotide sequence encoding a Cpf1 protein;
  wherein the guide RNA comprises from 1 to 50 additional nucleotides 5' of the stem loop; and
  wherein the guide RNA comprises from 1 to 50 additional nucleotides 3' of the guide segment.

In some aspects, disclosed herein is a genome editing system comprising:
  a) a guide RNA comprising a guide segment that hybridizes with a target sequence of a DNA molecule in a eukaryotic cell to form an RNA/DNA hybrid, and wherein the guide RNA forms a stem loop 5' of the RNA/DNA hybrid, and b) a Cpf1 protein;
wherein the guide RNA comprises from 1 to 50 additional nucleotides 5' of the stem loop.

In some aspects, disclosed herein is a genome editing system comprising:
a) a guide RNA comprising a guide segment that hybridizes with a target sequence of a DNA molecule in a eukaryotic cell to form an RNA/DNA hybrid, and wherein the guide RNA forms a stem loop 5' of the RNA/DNA hybrid, and
b) a Cpf1 protein;
wherein the guide RNA comprises from 1 to 50 additional nucleotides 5' of the stem loop; and
wherein the guide RNA comprises from 1 to 50 additional nucleotides 3' of the guide segment.

In some embodiments, the guide RNA and/or mRNA encoding a Cpf1 protein comprises at least one chemically modified nucleotide. In some embodiments, the at least one chemically modified nucleotide comprises a chemically modified nucleobase, a chemically modified ribose, a chemically modified phosphodiester linkage, or a combination thereof.

In some embodiments, the guide RNA and/or mRNA encoding a Cpf1 protein comprises at least one chemically modified nucleotide selected from a chemically modified nucleobase, a chemically modified ribose, a chemically modified phosphodiester linkage, or a combination thereof.

In some embodiments, the guide RNA and/or mRNA encoding a Cpf1 protein comprises at least one chemically modified nucleotide selected from a chemically modified nucleobase, a chemically modified ribose, a chemically modified phosphodiester linkage, or a combination thereof.

In some embodiments, the guide RNA and/or mRNA encoding a Cpf1 protein comprises at least one chemically modified nucleotide selected from a chemically modified nucleobase, a chemically modified ribose, a chemically modified phosphodiester linkage, or a combination thereof; and the guide RNA comprises at least one chemically modified nucleotide selected from a chemically modified nucleobase, a chemically modified ribose, a chemically modified phosphodiester linkage, or a combination thereof.

In some embodiments, the guide RNA and/or mRNA encoding a Cpf1 protein comprises a chemically modified nucleobase and the guide RNA comprises a chemically modified ribose.

In some embodiments, the guide RNA and/or mRNA encoding a Cpf1 protein comprises a pseudouridine (ψ) and the guide RNA comprises a chemically modified ribose.

In some embodiments, the guide RNA and/or mRNA encoding a Cpf1 protein comprises a chemically modified nucleobase and the guide RNA comprises a 2'-Fluoro (2'-F).

In some embodiments, the guide RNA and/or mRNA encoding a Cpf1 protein comprises a pseudouridine (ψ) and the guide RNA comprises a 2'-Fluoro (2'-F).

Methods

In some aspects, disclosed herein is a method of RNA-guided genome editing, the method comprising:
Introducing into a Cell of the Subject:
a) a guide RNA comprising a guide segment that hybridizes with a target sequence of a DNA molecule in a eukaryotic cell to form an RNA/DNA hybrid, and wherein the guide RNA forms a stem loop 5' of the RNA/DNA hybrid, and
b) an mRNA encoding a Cpf1 protein;
wherein the guide RNA comprises from 1 to 50 additional nucleotides 5' of the stem loop; and
wherein the guide RNA hybridizes with the target sequence and the Cpf1 protein cleaves the DNA molecule.

In other aspects, disclosed herein is a method of RNA-guided genome editing, the method comprising:
introducing into a cell of the subject:
a) a guide RNA comprising a guide segment that hybridizes with a target sequence of a DNA molecule in a eukaryotic cell to form an RNA/DNA hybrid, and wherein the guide RNA forms a stem loop 5' of the RNA/DNA hybrid, and
b) an mRNA encoding a Cpf1 protein;
wherein the guide RNA comprises from 1 to 50 additional nucleotides 5' of the stem loop;
wherein the guide RNA comprises from 1 to 50 additional nucleotides 3' of the guide segment;
and wherein the guide RNA hybridizes with the target sequence and the Cpf1 protein cleaves the DNA molecule.

In some aspects, disclosed herein is a method of RNA-guided genome editing, the method comprising:
Introducing into a Cell of the Subject:
a) a guide RNA comprising a guide segment that hybridizes with a target sequence of a DNA molecule in a eukaryotic cell to form an RNA/DNA hybrid, and wherein the guide RNA forms a stem loop 5' of the RNA/DNA hybrid, and
b) a DNA vector comprising a regulatory element operable in a eukaryotic cell operably linked to a nucleotide sequence encoding a Cpf1 protein;
wherein the guide RNA comprises from 1 to 50 additional nucleotides 5' of the stem loop; and
wherein the guide RNA hybridizes with the target sequence and the Cpf1 protein cleaves the DNA molecule.

In other aspects, disclosed herein is a method of RNA-guided genome editing, the method comprising:
Introducing into a Cell of the Subject:
a) a guide RNA comprising a guide segment that hybridizes with a target sequence of a DNA molecule in a eukaryotic cell to form an RNA/DNA hybrid, and wherein the guide RNA forms a stem loop 5' of the RNA/DNA hybrid, and
b) a DNA vector comprising a regulatory element operable in a eukaryotic cell operably linked to a nucleotide sequence encoding a Cpf1 protein;
wherein the guide RNA comprises from 1 to 50 additional nucleotides 5' of the stem loop;
wherein the guide RNA comprises from 1 to 50 additional nucleotides 3' of the guide segment;
and wherein the guide RNA hybridizes with the target sequence and the Cpf1 protein cleaves the DNA molecule.

In some aspects, disclosed herein is a method of RNA-guided genome editing, the method comprising:
Introducing into a Cell of the Subject:
a) a guide RNA comprising a guide segment that hybridizes with a target sequence of a DNA molecule in a eukaryotic cell to form an RNA/DNA hybrid, and wherein the guide RNA forms a stem loop 5' of the RNA/DNA hybrid, and
b) a Cpf1 protein;
wherein the guide RNA comprises from 1 to 50 additional nucleotides 5' of the stem loop; and
wherein the guide RNA hybridizes with the target sequence and the Cpf1 protein cleaves the DNA molecule.

In other aspects, disclosed herein is a method of RNA-guided genome editing, the method comprising:
Introducing into a Cell of the Subject:
- a) a guide RNA comprising a guide segment that hybridizes with a target sequence of a DNA molecule in a eukaryotic cell to form an RNA/DNA hybrid, and wherein the guide RNA forms a stem loop 5' of the RNA/DNA hybrid, and
- b) a Cpf1 protein;
wherein the guide RNA comprises from 1 to 50 additional nucleotides 5' of the stem loop;
wherein the guide RNA comprises from 1 to 50 additional nucleotides 3' of the guide segment; and wherein the guide RNA hybridizes with the target sequence and the Cpf1 protein cleaves the DNA molecule.

In some aspects, disclosed herein is a method of RNA-guided genome editing, the method comprising:
Introducing into a Cell of the Subject:
- a) a guide RNA comprising a guide segment that hybridizes with a target sequence of a DNA molecule in a eukaryotic cell to form an RNA/DNA hybrid, and wherein the guide RNA forms a stem loop 5' of the RNA/DNA hybrid, and
- b) a DNA vector comprising a regulatory element operable in a eukaryotic cell operably linked to a nucleotide sequence encoding a Cpf1 protein; an mRNA encoding a Cpf1 protein; or a Cpf1 protein;
wherein the guide RNA comprises from 1 to 50 additional nucleotides 5' of the stem loop; and
wherein the guide RNA comprises at least one chemically modified nucleotide.

In some embodiments, the guide RNA comprises a sequence selected from SEQ ID NO:1, SEQ ID NO: 2, SEQ ID NO:3, SEQ ID NO:4, SEQ ID NO:5, SEQ ID NO:6, SEQ ID NO:7, SEQ ID NO: 8, SEQ ID NO:9, SEQ ID NO: 10, SEQ ID NO:11, SEQ ID NO: 12, SEQ ID NO: 13, SEQ ID NO: 14, SEQ ID NO:15, or SEQ ID NO:16.

In some embodiments, the guide RNA comprises a sequence selected from SEQ ID NO:17, SEQ ID NO: 18, SEQ ID NO: 19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, or SEQ ID NO:32.

In some embodiments, the guide RNA comprises a sequence selected from SEQ ID NO:34, SEQ ID NO:35, SEQ ID NO:36, SEQ ID NO:37, SEQ ID NO:38, or SEQ ID NO:39.

In some embodiments, the guide RNA comprises a sequence selected from SEQ ID NO:40, SEQ ID NO:41, SEQ ID NO:42, SEQ ID NO:43, SEQ ID NO:44, or SEQ ID NO:45.

In some embodiments, the guide RNA comprises a 5' extension sequence and a stem loop sequence. In some embodiments, the guide RNA comprises a 5' extension sequence. In some embodiments, the guide RNA comprises a 5' extension sequence selected from Table 2. In some embodiments, the guide RNA comprises a 5' extension sequence selected from SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, or SEQ ID NO:61.

In some embodiments, the guide RNA comprises a stem loop sequence. In some embodiments, the guide RNA comprises a stem loop sequence selected from Table 2. In some embodiments, the guide RNA comprises a stem loop sequence selected from SEQ ID NO:62, SEQ ID NO: 63, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO: 72, SEQ ID NO: 73, SEQ ID NO: 74, SEQ ID NO:75, SEQ ID NO:76, or SEQ ID NO:77.

In some embodiments, the guide RNA comprises a 5' extension sequence selected from SEQ ID NO:46 to SEQ ID NO:61 and a stem loop sequence selected from SEQ ID NO:62 to SEQ ID NO: 77. Thus, the various 5' extension sequences from various species can be combined with any of the stem loop sequences from any of the species listed in Tables 1, 2, and 3. In addition, these guide RNA sequences may have additional 5' extensions and 3' extensions. In some embodiments, the guide RNA comprises at least one chemically modified nucleotide. In some embodiments, the at least one chemically modified nucleotide comprises a chemically modified nucleobase, a chemically modified ribose, a chemically modified phosphodiester linkage, or a combination thereof.

In some embodiments, the guide RNA comprises a nucleic acid which is at least 60%, at least 75%, at least 80%, at least 85%, at least 90%, at least 95%, at least 97.5%, or at least 99% identical to SEQ ID NO:1, SEQ ID NO:2, SEQ ID NO:3, SEQ ID NO:4, SEQ ID NO:5, SEQ ID NO: 6, SEQ ID NO:7, SEQ ID NO:8, SEQ ID NO:9, SEQ ID NO:10, SEQ ID NO:11, SEQ ID NO: 12, SEQ ID NO:13, SEQ ID NO:14, SEQ ID NO:15, or SEQ ID NO:16.

In some embodiments, the guide RNA comprises a nucleic acid which is at least 60%, at least 75%, at least 80%, at least 85%, at least 90%, at least 95%, at least 97.5%, or at least 99% identical to SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, or SEQ ID NO:32.

In some embodiments, the guide RNA comprises a nucleic acid which is at least 60%, at least 75%, at least 80%, at least 85%, at least 90%, at least 95%, at least 97.5%, or at least 99% identical to SEQ ID NO:34, SEQ ID NO:35, SEQ ID NO:36, SEQ ID NO:37, SEQ ID NO:38, or SEQ ID NO:39.

In some embodiments, the guide RNA comprises a nucleic acid which is at least 60%, at least 75%, at least 80%, at least 85%, at least 90%, at least 95%, at least 97.5%, or at least 99% identical to SEQ ID NO:40, SEQ ID NO:41, SEQ ID NO:42, SEQ ID NO:43, SEQ ID NO:44, or SEQ ID NO:45.

In some embodiments, the guide RNA comprises a nucleic acid which is at least 60%, at least 75%, at least 80%, at least 85%, at least 90%, at least 95%, at least 97.5%, or at least 99% identical to SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, or SEQ ID NO:61.

In some embodiments, the guide RNA comprises a nucleic acid which is at least 60%, at least 75%, at least 80%, at least 85%, at least 90%, at least 95%, at least 97.5%, or at least 99% identical to SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO: 70, SEQ ID NO:71, SEQ ID NO:72, SEQ ID NO:73, SEQ ID NO:74, SEQ ID NO:75, SEQ ID NO:76, or SEQ ID NO:77.

In some embodiments, the guide RNA comprises a 5' extension sequence selected from SEQ ID NO:46 to SEQ ID NO:61 and a stem loop sequence selected from SEQ ID NO:62 to SEQ ID NO: 77. Thus, the various 5' extension sequences from various species can be combined with any of the stem loop sequences from any of the species listed in Tables 1, 2, and 3. In addition, these guide RNA sequences may have additional 5' extensions and 3' extensions. In some embodiments, the guide RNA comprises at least one chemically modified nucleotide. In some embodiments, the at least one chemically modified nucleotide comprises a chemically modified nucleobase, a chemically modified ribose, a chemically modified phosphodiester linkage, or a combination thereof.

In some embodiments, the guide RNA further comprises from 10 to 40 nucleotides 5' of the stem loop. In some embodiments, the guide RNA further comprises from 20 to 30 nucleotides 5' of the stem loop.

In some embodiments, the guide RNA comprises from 1 to 50 additional nucleotides 3' (downstream) of a guide segment.

In some embodiments, the additional nucleotides 5' of the stem loop are heterologous nucleotides. In some embodiments, the heterologous nucleotides comprise a second RNA sequence from a different species compared to the guide segment, the stem loop, and/or the RNA/DNA hybrid.

In some embodiments, the method further comprises: introducing into a cell of the subject a guide RNA comprising a guide segment that hybridizes with a target sequence of a DNA molecule in a eukaryotic cell that contains the DNA molecule. The RNA/DNA hybrid is formed by the binding of a guide RNA sequence with a target DNA sequence (the RNA is complementary to and hybridizes to the target DNA sequence).

Previous studies have reported that chemical modifications can improve the stability and potency of various RNAs including siRNA, miRNA and antisense nucleic acids. Recently, chemical modifications were incorporated into guide RNAs for the CRISPR-Cas9 system comprising 2'O-methyl, 3'phosphorothioate, or 3'thioPACE at three terminal nucleotides at both the 5' and 3' ends of gRNAs (Hendel, A. *Nature Biotechnology* 2015, 33:985-989). In some embodiments, the guide RNA comprises at least one chemically modified nucleotide.

In some embodiments, the guide RNA and/or mRNA encoding a Cpf1 protein comprises at least one chemically modified nucleotide. In some embodiments, the at least one chemically modified nucleotide comprises a chemically modified nucleobase, a chemically modified ribose, a chemically modified phosphodiester linkage, or a combination thereof.

In some embodiments, the guide RNA and/or mRNA encoding a Cpf1 protein comprises at least one chemically modified nucleotide selected from a chemically modified nucleobase, a chemically modified ribose, a chemically modified phosphodiester linkage, or a combination thereof.

In some embodiments, the guide RNA and/or mRNA encoding a Cpf1 protein comprises at least one chemically modified nucleotide selected from a chemically modified nucleobase, a chemically modified ribose, a chemically modified phosphodiester linkage, or a combination thereof.

In some embodiments, the guide RNA and/or mRNA encoding a Cpf1 protein comprises at least one chemically modified nucleotide selected from a chemically modified nucleobase, a chemically modified ribose, a chemically modified phosphodiester linkage, or a combination thereof; and the guide RNA comprises at least one chemically modified nucleotide selected from a chemically modified nucleobase, a chemically modified ribose, a chemically modified phosphodiester linkage, or a combination thereof.

In some embodiments, the guide RNA and/or mRNA encoding a Cpf1 protein comprises a chemically modified nucleobase and the guide RNA comprises a chemically modified ribose. In some embodiments, the guide RNA and/or mRNA encoding a Cpf1 protein comprises a pseudouridine (ψ) and the guide RNA comprises a chemically modified ribose.

In some embodiments, the guide RNA and/or mRNA encoding a Cpf1 protein comprises a chemically modified nucleobase and the guide RNA comprises a 2'-Fluoro (2'-F).

In some embodiments, the guide RNA and/or mRNA encoding a Cpf1 protein comprises a pseudouridine (ψ) and the guide RNA comprises a 2'-Fluoro (2'-F).

Chemically Modified Nucleotides

In some embodiments, the at least one chemically modified nucleotide is a chemically modified nucleobase. In some embodiments, the mRNA encoding a Cpf1 protein comprises a chemically modified nucleobase. In some embodiments, the guide RNA comprises a chemically modified nucleobase.

In some embodiments, the chemically modified nucleobase is selected from 5-formylcytidine (5fC), 5-methylcytidine (5meC), 5-methoxycytidine (5moC), 5-hydroxycytidine (5hoC), 5-hydroxymethylcytidine (5hmC), 5-formyluridine (5fU), 5-methyluridine (5-meU), 5-methoxyuridine (5moU), 5-carboxymethylesteruridine (5camU), pseudouridine (ψ), $N^1$-methylpseudouridine (me$^1$ψ), $N^6$-methyladenosine (me$^6$A), or thienoguanosine ($^{th}$G).

In some embodiments, the chemically modified nucleobase is selected from 5-methoxyuridine (5moU), pseudouridine (ψ), and $N^1$-methylpseudouridine (me$^1$ψ). In some embodiments, the chemically modified nucleobase is 5-methoxyuridine (5moU). In some embodiments, the chemically modified nucleobase is pseudouridine (ψ). In some embodiments, the chemically modified nucleobase is $N^1$-methylpseudouridine (me$^1$ψ).

In some embodiments, the at least one chemically modified nucleobase comprises $N^1$-methylpseudouridine (me$^1$ψ) and 5-methylcytidine (5meC). In some embodiments, the at least one chemically modified nucleobase comprises pseudouridine (ψ) and 5-methylcytidine (5meC). In some embodiments, the at least one chemically modified nucleobase comprises 5-methyluridine (5-meU) and 5-methoxycytidine (5moC). In some embodiments, the at least one chemically modified nucleobase comprises 5-methyluridine (5-meU) and 5-hydroxymethylcytidine (5hmC). The structures of these modified nucleobases are shown below:

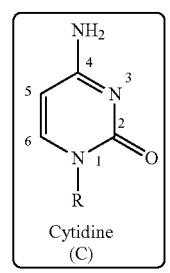
Cytidine (C)

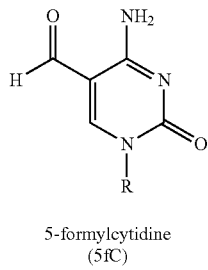
5-formylcytidine (5fC)

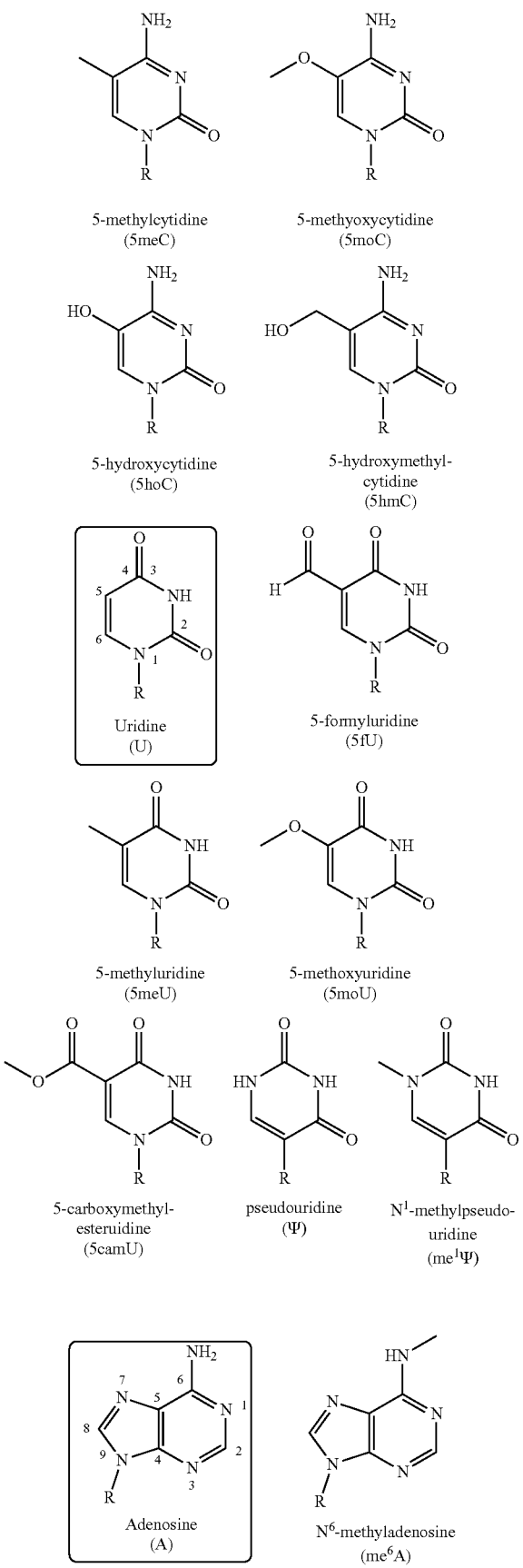

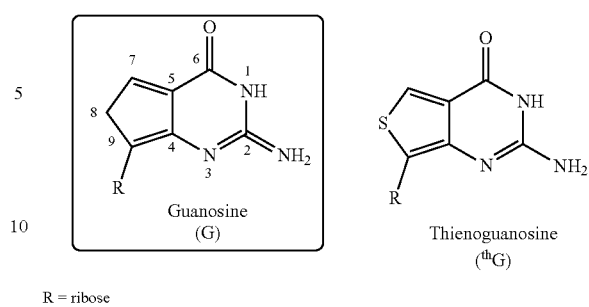

R = ribose

In some embodiments, the at least one chemically modified nucleotide is a chemically modified ribose. In some embodiments, the mRNA encoding a Cpf1 protein comprises a chemically modified ribose. In some embodiments, the guide RNA comprises a chemically modified ribose.

In some embodiments, the chemically modified ribose is selected from 2'-O-methyl (2'-O-Me), 2'-Fluoro (2'-F), 2'-deoxy-2'-fluoro-beta-D-arabino-nucleic acid (2'F-ANA), 4'-S, 4'-SFANA, 2'-azido, UNA, 2'-O-methoxy-ethyl(2'-O-ME), 2'-O-Allyl, 2'-O-Ethylamine, 2'-O-Cyanoethyl, Locked nucleic acid (LAN), Unlocked nucleic acid (UNA), Methylene-cLAN, N-MeO-amino BNA, or N-MeO-aminooxy BNA. In some embodiments, the chemically modified ribose is selected from 2'-O-methyl (2'-O-Me) or 2'-Fluoro (2'-F).

The structures of these modified riboses are shown below:

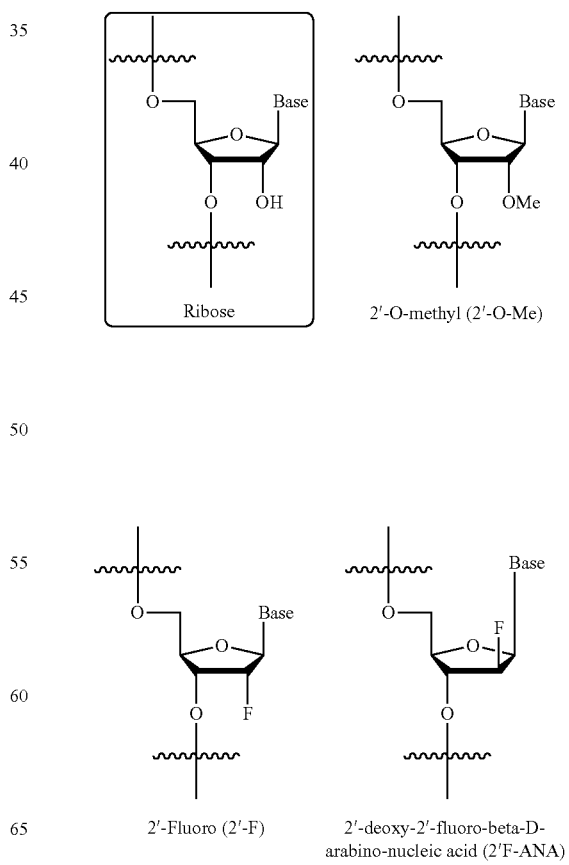

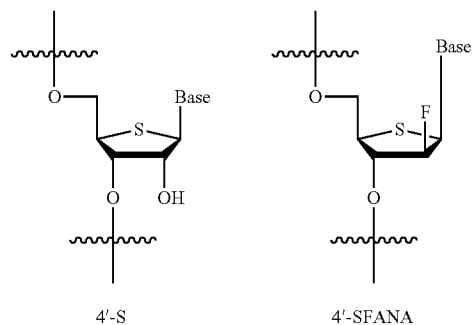

4'-S        4'-SFANA

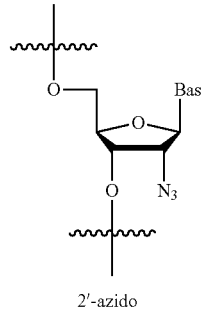 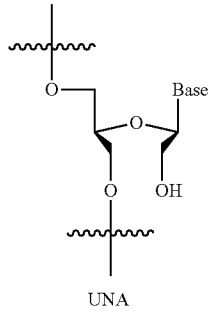

2'-azido        UNA

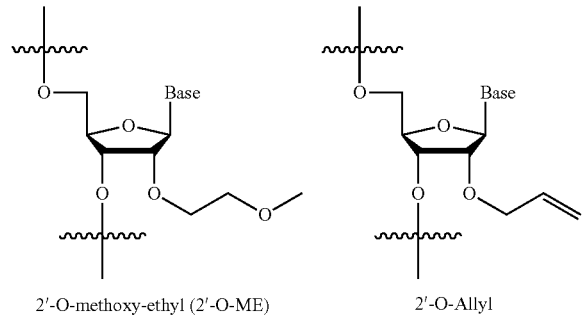

2'-O-methoxy-ethyl (2'-O-ME)        2'-O-Allyl

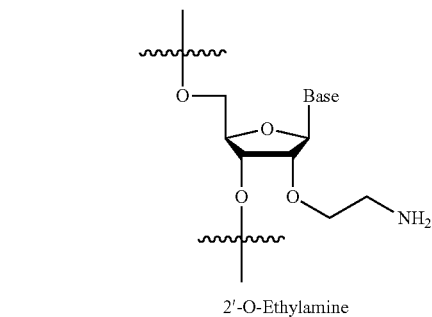

2'-O-Ethylamine

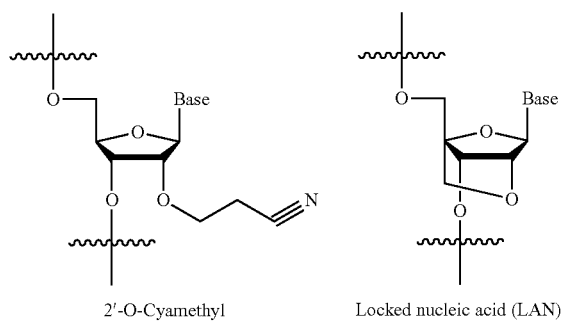

2'-O-Cyamethyl        Locked nucleic acid (LAN)

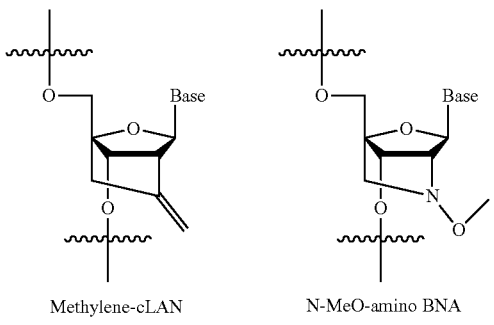

Methylene-cLAN        N-MeO-amino BNA

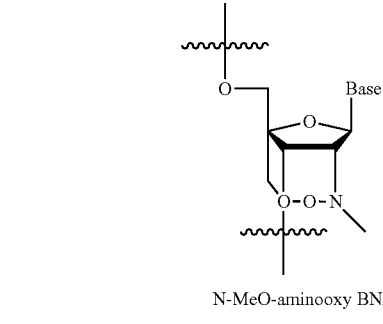

N-MeO-aminooxy BNA

In some embodiments, the at least one chemically modified nucleotide is a chemically modified phosphodiester linkage. In some embodiments, the mRNA encoding a Cpf1 protein comprises a chemically modified phosphodiester linkage. In some embodiments, the guide RNA comprises a chemically modified phosphodiester linkage.

In some embodiments, the chemically modified phosphodiester linkage is selected from Phosphorothioate (PS), Boranophosphate, phosphodithioate (PS2), 3',5'-amide, N3'-phosphoramidate (NP), Phosphodiester (PO), or 2',5'-phosphodiester (2',5'-PO). In some embodiments, the chemically modified phosphodiester linkage is phosphorothioate. The structures of these modified phosphodiester linkages are shown below:

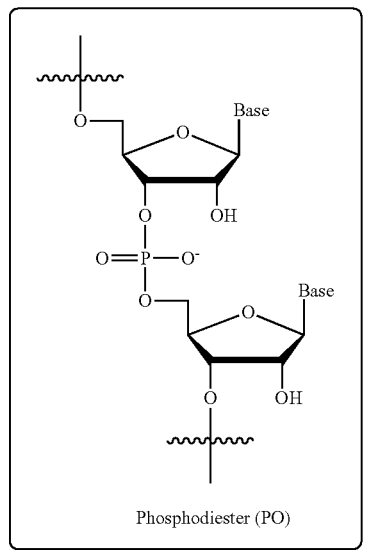

Phosphodiester (PO)

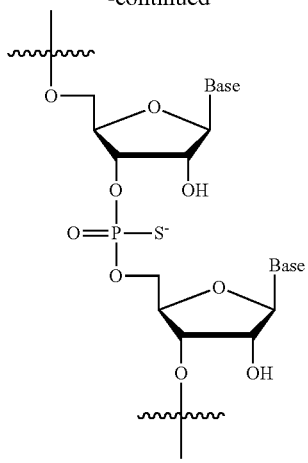
Phosporothioate (PS)
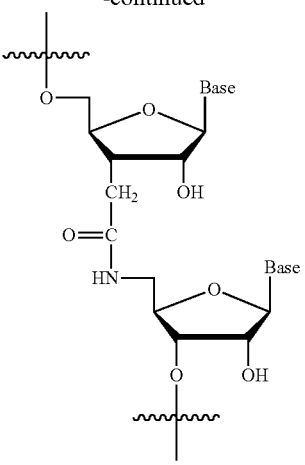
3', 5'-amide
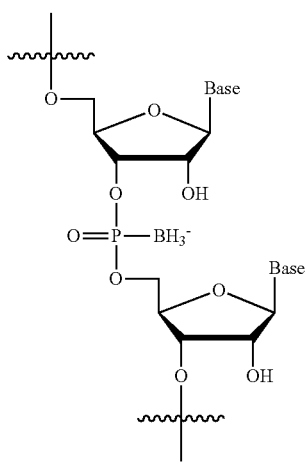
Boranophosphate
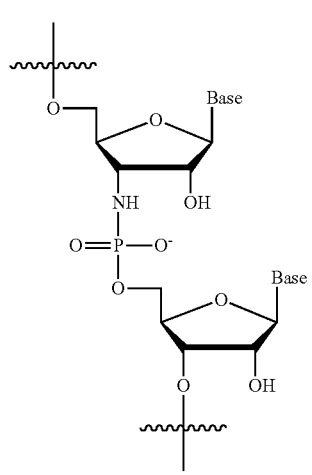
N3'-phosporamidate (NP)
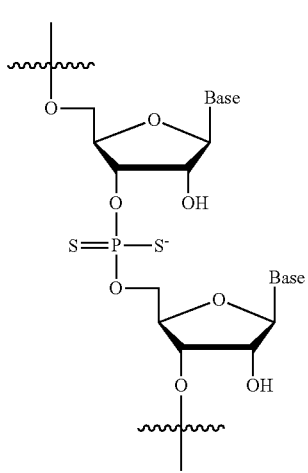
Phosphodithioate (PS2)
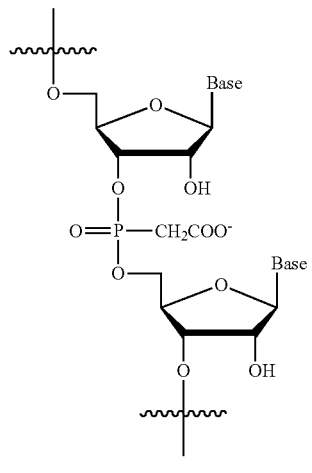
Phosphodiester (PO)

-continued

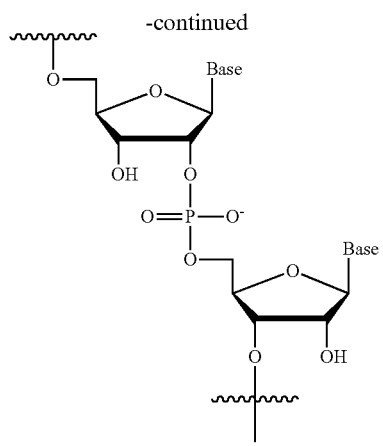

2', 5'-phosphodiester (2', 5'-PO)

In one aspect, the invention provides a kit comprising one or more of the components described herein. In some embodiments, the kit comprises instructions for using the kit. In some embodiments, the kit comprises:
a) a guide RNA comprising a guide segment that hybridizes with a target sequence of a DNA molecule in a eukaryotic cell to form an RNA/DNA hybrid, and wherein the guide RNA forms a stem loop 5' of the RNA/DNA hybrid, and
b) an mRNA encoding a Cpf1 protein;
wherein the guide RNA comprises from 1 to 50 additional nucleotides 5' of the stem loop;
wherein the mRNA encoding a Cpf1 protein comprises at least one chemically modified nucleotide, and
wherein the guide RNA hybridizes with the target sequence and the Cpf1 protein cleaves the DNA molecule.

In some embodiments, the invention provides a method of modifying a target polynucleotide in a eukaryotic cell. In some embodiments, the invention provides a method of modifying expression of a polynucleotide in a eukaryotic cell.

In some embodiments, an enzyme coding sequence encoding a Cpf1 protein is codon optimized for expression in particular cells, such as eukaryotic cells. In some embodiments, the DNA sequence encoding a Cpf1 protein is similar, or shares substantial identity with SEQ ID NO: 33. In some embodiments, the mRNA encoding a Cpf1 protein is encoded by SEQ ID NO:33. In some embodiments, the mRNA encoding a Cpf1 protein is encoded by a nucleic acid which is at least 60%, at least 75%, at least 80%, at least 85%, at least 90%, at least 95%, at least 97.5%, or at least 99% identical to SEQ ID NO:33.

In general, a guide RNA sequence or guide segment is any polynucleotide sequence having sufficient complementarity with a target polynucleotide sequence to hybridize with the target sequence and direct sequence-specific binding of a CRISPR-Cpf1 complex to the target sequence. In some embodiments, the degree of complementarity between a guide sequence or guide segment and its corresponding target sequence, when optimally aligned using a suitable alignment algorithm, is about or more than about 50%, 60%, 75%, 80%, 85%, 90%, 95%, 97.5%, 99%, or more. In some embodiments, the guide RNA comprises at least one chemically modified nucleotide.

Examples

The following examples are set forth below to illustrate the systems, methods, compositions and results according to the disclosed subject matter. These examples are not intended to be inclusive of all aspects of the subject matter disclosed herein, but rather to illustrate representative systems, methods, compositions and results. These examples are not intended to exclude equivalents and variations of the present invention which are apparent to one skilled in the art.

Example 1. Engineered Guide RNA

Figure 1:
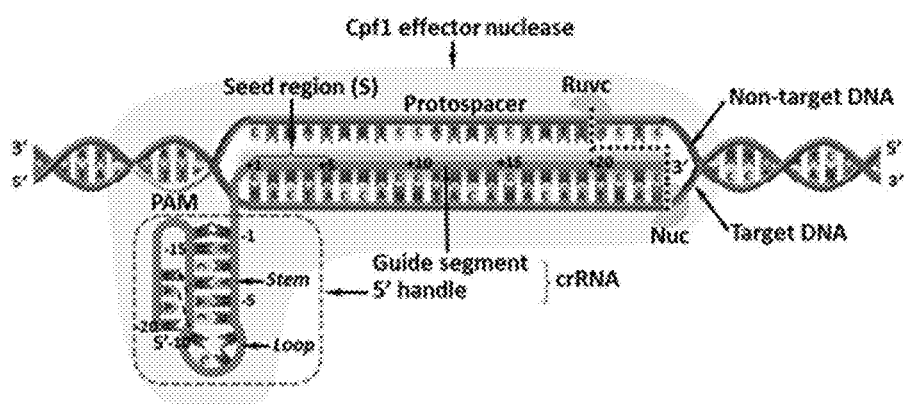
FIG. 1. Schematic illustration of AsCpf1-crRNA-target DNA complex and their terminology. crRNA is composed of a 5'-handle (in a pseudoknot structure) and a guide segment (consists of a seed region and 3'-termini). The dotted line denotes the cleavage sites.
Figure 2:
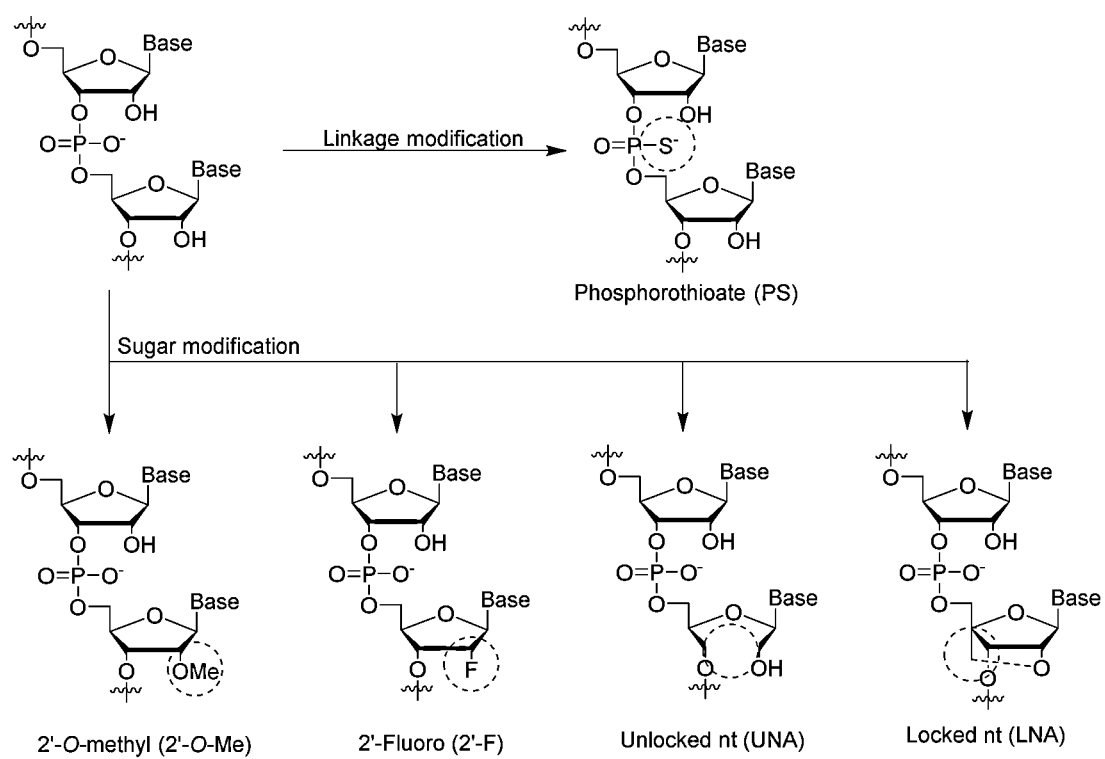
FIG. 2. Schematic diagram depicting chemical modifications applied to CRISPR-Cpf1 crRNAs. Modified positions (phosphate backbone and sugar modifications) of nucleotides were marked with the dotted circle.
Figure 3A:
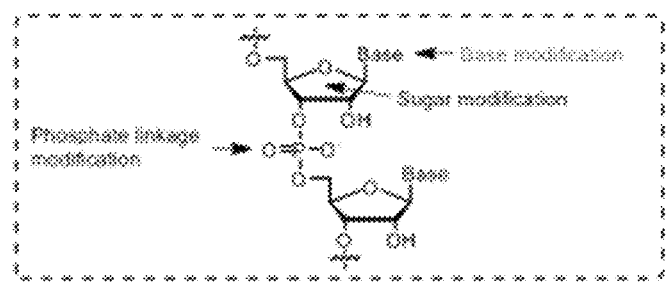
FIG. 3A-3D. A panel of chemically modified nucleotides utilized for engineering RNAs.
Figure 3B:
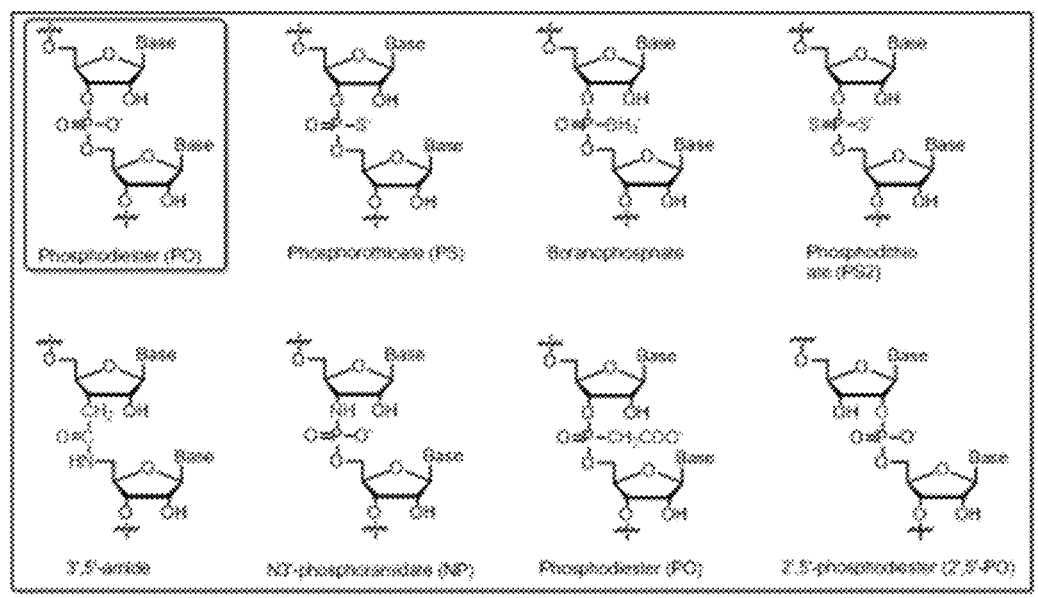
Figure 3C:
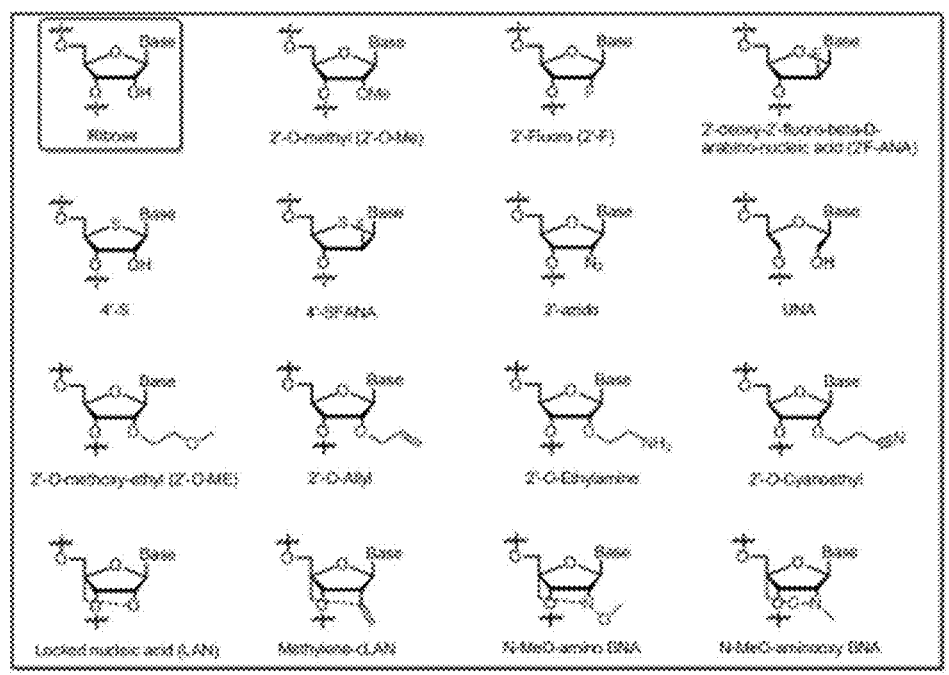
Figure 3D:
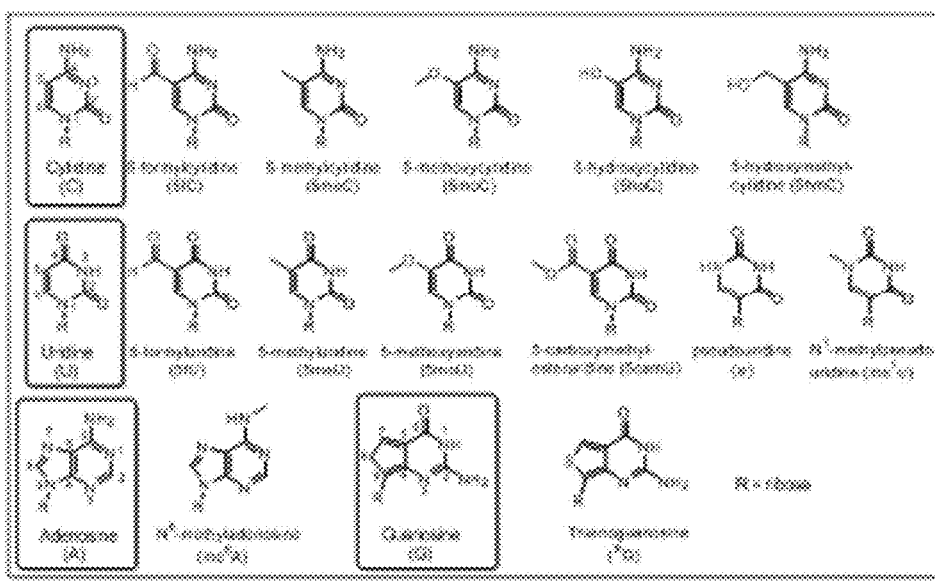

The guide RNAs disclosed in this example include 16 crRNA orthologues from 16 different species. The sequences of engineered crRNAs from 16 orthologues are shown in Table 1 (See SEQ ID NOs: 1 to 16). These sequences comprise up to 50 random nucleotides (included but not limited to highlighted sections that are integrated into the 5' end of the crRNA). Nucleotides of crRNAs can be modified with chemically modified nucleotides or their combination at 5'- or 3'-end, both ends, or the whole sequence (nucleotides included but not limited to those in FIG. 2, or FIG. 3). "X" denotes optional random nucleotides. "N" denotes a guide segment. "Y" denotes an optional 3'-extension, including up to 50 complimentary or random nucleotides. Engineered crRNAs also include multiple-repeated units of the crRNAs in the table. In addition, the 5'extensions could be any sequences from other Cpf1 orthologues or random sequences. For example, crRNA of Ascpf1 can use the 5'extension sequence of Lbcpf1 crRNA.

TABLE 1

Sequences of engineered guide RNAs (crRNAs)

| Seq. | Species | Guide RNA Sequence |
|---|---|---|
| SEQ ID NO: 1 | FnCpf1 crRNA | 5'-XXXXXGUCUAAGAACUUUAAAUAAUUUCUACUGUUGUAGAUNNNNNNNNNNNNNNNNNNNNNNNNNY-3' |
| SEQ ID NO: 2 | Lb3Cpf1 crRNA | 5'-XXXXXGUUUUGGAGUACCUUAGAAAUGCAUGGUUCUCAUGCNNNNNNNNNNNNNNNNNNNNNNNNNY-3' |
| SEQ ID NO: 3 | BpCpf1 crRNA | 5'-XXXXXGUUUUAGAACCUUAAAAAUUACCUAGUAAUUAGGUNNNNNNNNNNNNNNNNNNNNNNNNNY-3' |
| SEQ ID NO: 4 | PeCpf1 crRNA | 5'-XXXXXGUUUAAAAGUCCUAUUGGAUUUCUACUUUUGUAGAUNNNNNNNNNNNNNNNNNNNNNNNNNY-3' |
| SEQ ID NO: 5 | PbCpf1 crRNA | 5'-XXXXXGCCAAAUACCUCUAUAAAAUUUCUACUUUUGUAGAUNNNNNNNNNNNNNNNNNNNNNNNNNY-3' |

TABLE 1-continued

Sequences of engineered guide RNAs (crRNAs)

| Seq. | Species | Guide RNA Sequence |
|---|---|---|
| SEQ ID NO: 6 | SsCpf1 crRNA | 5'-XXXXXGUUUCAAUCCACGCGCCCACGCGGGGCGCGACNNNNNNNNNNNNNNNNNNNNNNNNY-3' |
| SEQ ID NO: 7 | AsCpf1 crRNA | 5'-XXXXXGUCAAAAGACCUUUUUAAUUUCUACUCUUGUAGAUNNNNNNNNNNNNNNNNNNNNNNNNY-3' |
| SEQ ID NO: 8 | Lb2Cpf1 crRNA | 5'-XXXXXGCUUAGAACAUUUAAAGAAUUUCUACUAUUGUAGAUNNNNNNNNNNNNNNNNNNNNNNNNY-3' |
| SEQ ID NO: 9 | CmtCpf1 crRNA | 5'-XXXXXCUCAAAACUCAUUCGAAUCUCUACUCUUUGUAGAUNNNNNNNNNNNNNNNNNNNNNNNNY-3' |
| SEQ ID NO: 10 | EeCpf1 crRNA | 5'-XXXXXGUUUGAAUAACCUUAAAUAAUUUCUACUUUGUAGAUNNNNNNNNNNNNNNNNNNNNNNNNY-3' |
| SEQ ID NO: 11 | MbCpf1 crRNA | 5'-XXXXXGUCUAACGACCUUUUAAAUUUCUACUGUUUGUAGAUNNNNNNNNNNNNNNNNNNNNNNNNY-3' |
| SEQ ID NO: 12 | LiCpf1 crRNA | 5'-XXXXXCUCUAAAGAGAGGAAAGAAUUUCUACUUUUGUAGAUNNNNNNNNNNNNNNNNNNNNNNNNY-3' |
| SEQ ID NO: 13 | LbCpf1 crRNA | 5'-XXXXXGUUUCAAAGAUUAAAUAAUUUCUACUAAGUGUAGAUNNNNNNNNNNNNNNNNNNNNNNNNY-3' |
| SEQ ID NO: 14 | PcCpf1 crRNA | 5'-XXXXXGUCUAGGUACUCUCUUUAAUUUCUACUAUUGUAGAUNNNNNNNNNNNNNNNNNNNNNNNNY-3' |
| SEQ ID NO: 15 | PdCpf1 crRNA | 5'-XXXXXGUCAAUAAGACUCAUUUAAUUUCUACUUCGGUAGAUNNNNNNNNNNNNNNNNNNNNNNNNY-3' |
| SEQ ID NO: 16 | PmCpf1 crRNA | 5'-XXXXXGCCUAUAAGGCUUUAGUAAUUUCUACUAUUGUAGAUNNNNNNNNNNNNNNNNNNNNNNNNY-3' |
| SEQ ID NO: 17 | FnCpf1 crRNA | 5'-GUCUAAGAACUUUAAAUAAUUUCUACUGUUGUAGAU-3' |
| SEQ ID NO: 18 | Lb3Cpf1 crRNA | 5'-GUUUUGGAGUACCUUAGAAAUGCAUGGUUCUCAUGC-3' |
| SEQ ID NO: 19 | BpCpf1 crRNA | 5'-GUUUUAGAACCUUAAAAAUUACCUAGUAAUUAGGU-3' |
| SEQ ID NO: 20 | PeCpf1 crRNA | 5'-GUUUAAAAGUCCUAUUGGAUUUCUACUUUUGUAGAU-3' |
| SEQ ID NO: 21 | PbCpf1 crRNA | 5'-GCCAAAUACCUCUAUAAAAUUUCUACUUUUGUAGAU-3' |
| SEQ ID NO: 22 | SsCpf1 crRNA | 5'-GUUUCAAUCCACGCGCCCACGCGGGGCGCGAC-3' |
| SEQ ID NO: 23 | AsCpf1 crRNA | 5'-GUCAAAAGACCUUUUUAAUUUCUACUCUUGUAGAU-3' |
| SEQ ID NO: 24 | Lb2Cpf1 crRNA | 5'-GCUUAGAACAUUUAAAGAAUUUCUACUAUUGUAGAU-3' |
| SEQ ID NO: 25 | CmtCpf1 crRNA | 5'-CUCAAAACUCAUUCGAAUCUCUACUCUUUGUAGAU-3' |
| SEQ ID NO: 26 | EeCpf1 crRNA | 5'-GUUUGAAUAACCUUAAAUAAUUUCUACUUUGUAGAU-3' |
| SEQ ID NO: 27 | MbCpf1 crRNA | 5'-GUCUAACGACCUUUUAAAUUUCUACUGUUUGUAGAU-3' |
| SEQ ID NO: 28 | LiCpf1 crRNA | 5'-CUCUAAAGAGAGGAAAGAAUUUCUACUUUUGUAGAU-3' |
| SEQ ID NO: 29 | LbCpf1 crRNA | 5'-GUUUCAAAGAUUAAAUAAUUUCUACUAAGUGUAGAU-3' |
| SEQ ID NO: 30 | PcCpf1 crRNA | 5'-GUCUAGGUACUCUCUUUAAUUUCUACUAUUGUAGAU-3' |

TABLE 1-continued

Sequences of engineered guide RNAs (crRNAs)

| Seq. | Species | Guide RNA Sequence |
|---|---|---|
| SEQ ID NO: 31 | PdCpf1 crRNA | 5'-GUCAAUAAGACUCAUUUAAUUUCUACUUCGGUAGAU-3' |
| SEQ ID NO: 32 | PmCpf1 crRNA | 5'-GCCUAUAAGGCUUUAGUAAUUUCUACUAUUGUAGAU-3' |

From the sequences disclosed in Table 1, the 5' extension sequence may be selected from, for example, SEQ ID NO:46 to SEQ ID NO:61 and the stem loop sequence may be selected from, for example, SEQ ID NO:62 to SEQ ID NO:77.

TABLE 2

5'extension sequences and stem loop sequences

| Seq. | Species | RNA Sequence |
|---|---|---|
| SEQ ID NO: 46 | FnCpf1 crRNA | 5'-GUCUAAGAACUUUAAA-3' |
| SEQ ID NO: 47 | Lb3Cpf1 crRNA | 5'-GUUUUGGAGUACCUU-3' |
| SEQ ID NO: 48 | BpCpf1 crRNA | 5'-GUUUUAGAACCUUA-3' |
| SEQ ID NO: 49 | PeCpf1 crRNA | 5'-GUUUAAAAGUCCUAUU-3' |
| SEQ ID NO: 50 | PbCpf1 crRNA | 5'-GCCAAAUACCUCUAUA-3' |
| SEQ ID NO: 51 | SsCpf1 crRNA | 5'-GUUUCAAUCCA-3' |
| SEQ ID NO: 52 | AsCpf1 crRNA | 5'-GUCAAAAGACCUUUU-3' |
| SEQ ID NO: 53 | Lb2Cpf1 crRNA | 5'-GCUUAGAACAUUUAAA-3' |
| SEQ ID NO: 54 | CmtCpf1 crRNA | 5'-CUCAAAACUCAUUC-3' |
| SEQ ID NO: 55 | EeCpf1 crRNA | 5'-GUUUGAAUAACCUUAAA-3' |
| SEQ ID NO: 56 | MbCpf1 crRNA | 5'-GUCUAACGACCUUUU-3' |
| SEQ ID NO: 57 | LiCpf1 crRNA | 5'-CUCUAAAGAGAGGAAA-3' |
| SEQ ID NO: 58 | LbCpf1 crRNA | 5'-GUUUCAAAGAUUAAA-3' |
| SEQ ID NO: 59 | PcCpf1 crRNA | 5'-GUCUAGGUACUCUCUU-3' |
| SEQ ID NO: 60 | PdCpf1 crRNA | 5'-GUCAAUAAGACUCAUU-3' |
| SEQ ID NO: 61 | PmCpf1 crRNA | 5'-GCCUAUAAGGCUUUAG-3' |
| SEQ ID NO: 62 | FnCpf1 crRNA | UAAUUUCUACUGUUGUAGAU |
| SEQ ID NO: 63 | Lb3Cpf1 crRNA | AGAAAUGCAUGGUUCUCAUGC |
| SEQ ID NO: 64 | BpCpf1 crRNA | AAAAUUACCUAGUAAUUAGGU |
| SEQ ID NO: 65 | PeCpf1 crRNA | GGAUUUCUACUUUUGUAGAU |
| SEQ ID NO: 66 | PbCpf1 crRNA | AAAUUUCUACUUUUGUAGAU |
| SEQ ID NO: 67 | SsCpf1 crRNA | CGCGCCCACGCGGGGCGCGAC |
| SEQ ID NO: 68 | AsCpf1 crRNA | UAAUUUCUACUCUUGUAGAU |
| SEQ ID NO: 69 | Lb2Cpf1 crRNA | GAAUUUCUACUAUUGUAGAU |
| SEQ ID NO: 70 | CmtCpf1 crRNA | GAAUCUCUACUCUUUGUAGAU |
| SEQ ID NO: 71 | EeCpf1 crRNA | UAAUUUCUACUUUUGUAGAU |
| SEQ ID NO: 72 | MbCpf1 crRNA | AAAUUUCUACUGUUUGUAGAU |
| SEQ ID NO: 73 | LiCpf1 crRNA | GAAUUUCUACUUUUGUAGAU |
| SEQ ID NO: 74 | LbCpf1 crRNA | UAAUUUCUACUAAGUGUAGAU |
| SEQ ID NO: 75 | PcCpf1 crRNA | UAAUUUCUACUAUUGUAGAU |
| SEQ ID NO: 76 | PdCpf1 crRNA | UAAUUUCUACUUCGGUAGAU |
| SEQ ID NO: 77 | PmCpf1 crRNA | UAAUUUCUACUAUUGUAGAU |

Note that the RNA sequences disclosed in Tables 1 and 2 can comprise at least one chemically modified nucleotide, as described in the specification above.

Example 2. Genome Editing by Engineered Guide RNAs

Figure 4:
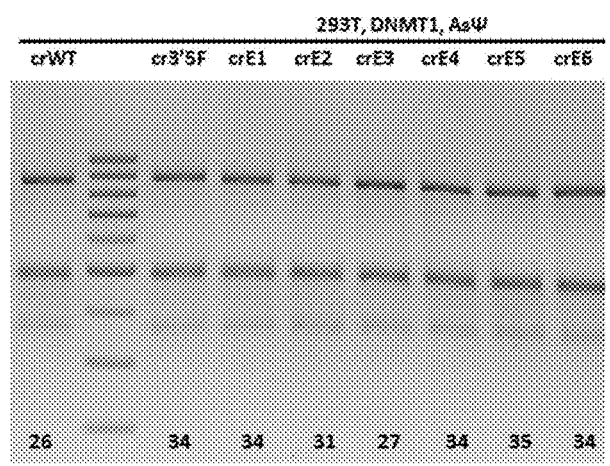
FIG. 4. T7E1 cleavage assay measuring the gene editing efficiency by engineered guide RNAs. Sequences used in the T7E1 cleavage assay are shown in the table accompanying the photograph of the representative gel.

FIG. 4 shows the T7E1 cleavage assay measuring the gene editing efficiency by engineered guide RNAs. Sequences used in the T7E1 cleavage assay in FIG. 4 are shown in Table 3 below.

TABLE 3

Sequences of engineered guide RNAs (crRNAs) used in this example

| Seq. | Name | Oligo Name | Guide RNA Sequence |
|---|---|---|---|
| SEQ ID NO: 34 | crE1 | cr5'3F&3'5F(GGG) | 5'-<u>GGG</u>UAAUUUCUACUCUUGUAGAUCUGAUGGUCCAUGUCUGUU<u>ACUC</u>-3' |
| SEQ ID NO: 35 | crE2 | cr5'3M2P5&3'5F(GGG) | 5'-GGGUAAUUUCUACUCUUGUAGAUCUGAUGGUCCAUGUCUGUU<u>ACUC</u>-3' |
| SEQ ID NO: 36 | crE3 | cr5'3F&3'5F(UUU) | 5'-<u>UUU</u>UAAUUUCUACUCUUGUAGAUCUGAUGGUCCAUGUCUGUU<u>ACUC</u>-3' |
| SEQ ID NO: 37 | crE4 | cr5'3M2P5&3'5F(UUU) | 5'-UUUUAAUUUCUACUCUUGUAGAUCUGAUGGUCCAUGUCUGUU<u>ACUC</u>-3' |
| SEQ ID NO: 38 | crE5 | cr5'5F&3'5F(CUUUU) | 5'-<u>CUUUU</u>UAAUUUCUACUCUUGUAGAUCUGAUGGUCCAUGUCUGUU<u>ACUC</u>-3' |
| SEQ ID NO: 39 | crE6 | cr5'5M2PS&3'5F(CUUUU) | 5'-CUUUUUAAUUUCUACUCUUGUAGAUCUGAUGGUCCAUGUCUGUU<u>ACUC</u>-3' |

Underlined sequences in Table 3 represent nucleotides with a modified with a 2'-Fluror (2'-F) chemically modified ribose.
Bold sequences in Table 3 represent nucleotides with a 2'-O-methyl (2'-O-Me) chemically modified ribose and a phosphorothioate (PS) chemically modified phosphodiester linkage.

Thus, in this example the stem loop sequence (UAAUUUC-UACUCUUGUAGAU (SEQ ID NO: 68)), is used with the 5' extensions that have been modified with a 2'-Fluoro (2'-F), a 2'-O-methyl (2'-O-Me) chemically modified ribose, or a phosphorothioate (PS). The guide segment comprises CUGAUGGUCCAUGUCUGU (SEQ ID NO:78), and the last 5 nucleotides are modified with a 2'-Fluoro (2'-F).

Co-Delivery of AsCpf1 mRNA & Guide RNA (gRNA) and Extraction of Genomic DNA 293T cells were seeded on a 24-well plate at a density of 100,000 cells per well. After overnight culture, cells were treated with AsCpf1 mRNA expressing AsCpf1 protein (500 or 1000 ng) and engineered gRNA (15 or 30 μmol, PAGE-grade) using LipofectamineMAX, Lipofectamine 3000 or mRNA—in reagent. 48 hr after treatment, genomic DNA (gDNA) from 293T cells was extracted using the DNeasy Blood & Tissue Kit (QIAGEN) following the manufacturer's instructions, and quantified by Nanodrop 2000. Unmodified guide RNA served as a control.

T7E1 Assay

On-target or off-target sites were amplified using Q5 High-Fidelity DNA Polymerase (New England Biolabs) and specific primers (Integrated DNA Technologies, Supplementary). The PCR products (10 uL) were then hybridized in NEBuffer 2 (New England Biolabs) in a T100 thermal cycler (Bio-Rad). Subsequently, the annealed PCR products were subjected to T7 Endonuclease I (New England Biolabs) digestion, and analysis on a 2% agarose gel to determine the efficiency of genome editing (indel %) with the following formula:

$$100 \times (1-(1-\text{fraction cleaved})^{1/2}).$$

Example 3. Increased Editing by Engineered Guide RNAs

Figure 5:
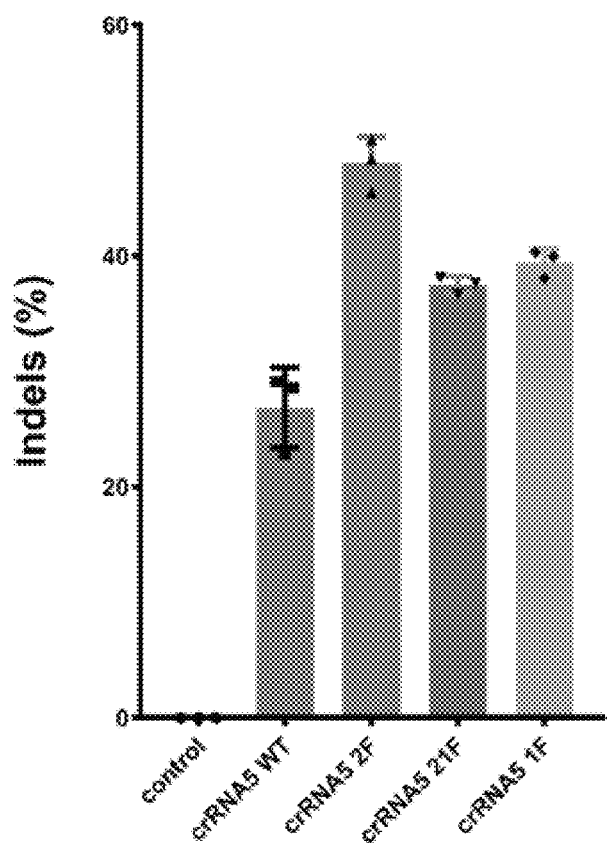
FIG. 5. Modified guide RNA (crRNA5 2F) significantly improved gene editing efficiency compared to the wild type guide RNA, IVT crTrp53 in stem cells. Sequences (Underlined sequences represent nucleotides with a modified with a 2'-Fluoro (2' F) chemically modified ribose)

FIG. 5 shows that modified guide RNA (crRNA5 2F) significantly improved gene editing efficiency compared to the wild type guide RNA, IVT crTrp53 in stem cells. Sequences used in FIG. 5 (Underlined sequences represent nucleotides with a modified with a 2'-Fluoro (2' F) chemically modified ribose):

IVT crRNA5:
(SEQ ID NO: 40)
5'-GGGUAAUUUCUACUCUUGUAGAUGGAUGUGUUCUUACCACAGAGGG-3' crRNA5 1F:
(SEQ ID NO: 41)
5'-UAAUUUCUACUCUUGUAGAUGGAUGUGUUCUUACCAC<u>AGAGG</u>G-3' crRNA5 2F:
(SEQ ID NO: 42)
5'-<u>CUUUU</u>GGGUAAUUUCUACUCUUGUAGAUGGAUGUGUUCUUACCAC<u>AGAGG</u>G-3' crRNA5 21F:
(SEQ ID NO: 43)
5'-<u>UAAUUUCUACUCUUGUAGAU</u>GGAUGUGUUCUUACC<u>ACAGAGG</u>G-3'

Thus, in this example the stem loop sequence (UAAUUUCUACUCUUGUAGAU (SEQ ID NO: 68)), is used with the 5' extensions and/or sequences that have been modified with a 2'-Fluoro (2'-F). The guide segment comprises GGAUGUGUUCUUACCACA (SEQ ID NO:79), and the last 5 nucleotides can be modified with a 2'-Fluoro (2'-F).

FIG. 6 shows that modified guide RNA (crTrp53 2F) significantly improved gene editing efficiency compared to the wild type guide RNA, IVT crTrp53 in the stem cells. Sequences used in FIG. 6 (Underlined sequences represent nucleotides with a modified with a 2'-Fluoro (2' F) chemically modified ribose):

IVT crTrp53:
(SEQ ID NO: 44)
5'-GGGUAAUUUCUACUCUUGUAGAUCUUCCACCCGGAUAAGAUGCUGG-3' crTrp53 2F:
(SEQ ID NO: 45)
5'-<u>CUUUU</u>UAAUUUCUACUCUUGUAGAUCUUCCACCCGGAUAAGAUGC<u>UGG</u>-3'

Thus, in this example the stem loop sequence (UAAUUUCUACUCUUGUAGAU (SEQ ID NO: 68)), is used with the 5' extensions and/or sequences that have been modified with a 2'-Fluoro (2'-F). The guide segment comprises CUUCCACCCGGAUAAGAU (SEQ ID NO:80), and the last 5 nucleotides can be modified with a 2'-Fluoro (2'-F).

Example 4. Synthesis of Cpf1 mRNA

Synthesis of chemically modified Cpf1 mRNA

Wild type and chemically modified mRNAs encoding AsCpf1 (Acidaminococcus sp. BV3L6 CRISPR from *Prevotella* and *Francisella* 1) protein including but not limited to PS backbone modification, ψ, 5moU, me$^1$ψ, 5hmC, 5meU, 5meC and 5moC base modification, 2'-O-Me, 2'-F sugar modification, as well as their combinations are synthesized using a commercially available in vitro transcription kit. All mRNA are verified by polyacrylamide gel electrophoresis (PAGE). These Cpf1 mRNAs can contain a complete replacement of the wild-type uridine nucleotides with either ψ, 5moU, or me$^1$ψ (See FIG. 3).

Cpf1 Protein

In some embodiments, the Cpf1 protein is encoded by SEQ ID NO:33. This sequence can be codon optimized, can differ due to the degeneracy of the genetic code, can be similar, or share substantial identity, to SEQ ID NO:33, but still retain nuclease activity. Other Cpf1 nucleases are known in the art and can be used as well. In some embodiments, all of the uridines (corresponding to the thymidines (T) in the DNA sequence) in the Cpf1 mRNA have been replaced by pseudouridine (See FIG. 3). In some embodiments, all of the uridines (corresponding to the thymidines (T) in the DNA sequence) in the Cpf1 mRNA have been replaced by N$_1$-methylpseudouridine (me$^1$ψ) (See FIG. 3). In some embodiments, all of the uridines (corresponding to the thymidines (T) in the DNA sequence) in the Cpf1 mRNA have been replaced by 5-methoxyuridine (5moU) (See FIG. 3).

```
Cpf1 sequence (SEQ ID NO: 33)
                                          (SEQ ID NO: 33)
ATGACACAGTTCGAGGGCTTTACCAACCTGTATCAGGTGAGCAAGACACT

GCGGTTTGAGCTGATCCCACAGGGCAAGACCCTGAAGCACATCCAGGAGC

AGGGCTTCATCGAGGAGGACAAGGCCCGCAATGATCACTACAAGGAGCTG

AAGCCCATCATCGATCGGATCTACAAGACCTATGCCGACCAGTGCCTGCA

GCTGGTGCAGCTGGATTGGGAGAACCTGAGCGCCGCCATCGACTCCTATA

GAAAGGAGAAAACCGAGGAGACAAGGAACGCCCTGATCGAGGAGCAGGCC

ACATATCGCAATGCCATCCACGACTACTTCATCGGCCGGACAGACAACCT

GACCGATGCCATCAATAAGAGACACGCCGAGATCTACAAGGGCCTGTTCA

AGGCCGAGCTGTTTAATGGCAAGGTGCTGAAGCAGCTGGGCACCGTGACC

ACAACCGAGCACGAGAACGCCCTGCTGCGGAGCTTCGACAAGTTTACAAC

CTACTTCTCCGGCTTTTATGAGAACAGGAAGAACGTGTTCAGCGCCGAGG

ATATCAGCACAGCCATCCCACACCGCATCGTGCAGGACAACTTCCCCAAG

TTTAAGGAGAATTGTCACATCTTCACACGCCTGATCACCGCCGTGCCCAG

CCTGCGGGAGCACTTTGAGAACGTGAAGAAGGCCATCGGCATCTTCGTGA

GCACCTCCATCGAGGAGGTGTTTTCCTTCCCTTTTTATAACCAGCTGCTG
```

-continued
```
ACACAGACCCAGATCGACCTGTATAACCAGCTGCTGGGAGGAATCTCTCG

GGAGGCAGGCACCGAGAAGATCAAGGGCCTGAACGAGGTGCTGAATCTGG

CCATCCAGAAGAATGATGAGACAGCCCACATCATCGCCTCCCTGCCACAC

AGATTCATCCCCCTGTTTAAGCAGATCCTGTCCGATAGGAACACCCTGTC

TTTCATCCTGGAGGAGTTTAAGAGCGACGAGGAAGTGATCCAGTCCTTCT

GCAAGTACAAGACACTGCTGAGAAACGAGAACGTGCTGGAGACAGCCGAG

GCCCTGTTTAACGAGCTGAACAGCATCGACCTGACACACATCTTCATCAG

CCACAAGAAGCTGGAGACAATCAGCAGCGCCCTGTGCGACCACTGGGATA

CACTGAGGAATGCCCTGTATGAGCGGAGAATCTCCGAGCTGACAGGCAAG

ATCACCAAGTCTGCCAAGGAGAAGGTGCAGCGCAGCCTGAAGCACGAGGA

TATCAACCTGCAGGAGATCATCTCTGCCGCAGGCAAGGAGCTGAGCGAGG

CCTTCAAGCAGAAAACCAGCGAGATCCTGTCCCACGCACACGCCGCCCTG

GATCAGCCACTGCCTACAACCCTGAAGAAGCAGGAGGAGAAGGAGATCCT

GAAGTCTCAGCTGGACAGCCTGCTGGGCCTGTACCACCTGCTGGACTGGT

TTGCCGTGGATGAGTCCAACGAGGTGGACCCCGAGTTCTCTGCCCGGCTG

ACCGGCATCAAGCTGGAGATGGAGCCTTCTCTGAGCTTCTACAACAAGGC

CAGAAATTATGCCACCAAGAAGCCCTACTCCGTGGAGAAGTTCAAGCTGA

ACTTTCAGATGCCTACACTGGCCTCTGGCTGGGACGTGAATAAGGAGAAG

AACAATGGCGCCATCCTGTTTGTGAAGAACGGCCTGTACTATCTGGGCAT

CATGCCAAAGCAGAAGGGCAGGTATAAGGCCCTGAGCTTCGAGCCCACAG

AGAAAACCAGCGAGGGCTTTGATAAGATGTACTATGACTACTTCCCTGAT

GCCGCCAAGATGATCCCAAAGTGCAGCACCCAGCTGAAGGCCGTGACAGC

CCACTTTCAGACCCACACAACCCCCATCCTGCTGTCCAACAATTTCATCG

AGCCTCTGGAGATCACAAAGGAGATCTACGACCTGAACAATCCTGAGAAG

GAGCCAAAGAAGTTTCAGACAGCCTACGCCAAGAAAACCGGCGACCAGAA

GGGCTACAGAGAGGCCCTGTGCAAGTGGATCGACTTCACAAGGGATTTTC

TGTCCAAGTATACCAAGACAACCTCTATCGATCTGTCTAGCCTGCGGCCA

TCCTCTCAGTATAAGGACCTGGGCGAGTACTATGCCGAGCTGAATCCCCT

GCTGTACCACATCAGCTTCCAGAGAATCGCCGAGAAGGAGATCATGGATG

CCGTGGAGACAGGCAAGCTGTACCTGTTCCAGATCTATAACAAGGACTTT

GCCAAGGGCCACCACGGCAAGCCTAATCTGCACACACTGTATTGGACCGG

CCTGTTTTCTCCAGAGAACCTGGCCAAGACAAGCATCAAGCTGAATGGCC

AGGCCGAGCTGTTCTACCGCCCTAAGTCCAGGATGAAGAGGATGGCACAC

CGGCTGGGAGAAGATGCTGAACAAGAAGCTGAAGGATCAGAAAACCCC

AATCCCCGACACCCTGTACCAGGAGCTGTACGACTATGTGAATCACAGAC

TGTCCCACGACCTGTCTGATGAGGCCAGGGCCCTGCTGCCCAACGTGATC

ACCAAGGAGGTGTCTCACGAGATCATCAAGGATAGGCGCTTTACCAGCGA

CAAGTTCTTTTTCCACGTGCCTATCACACTGAACTATCAGGCCGCCAATT

CCCCATCTAAGTTCAACCAGAGGGTGAATGCCTACCTGAAGGAGCACCCC

GAGACACCTATCATCGGCATCGATCGGGGCGAGAGAAACCTGATCTATAT

CACAGTGATCGACTCCACCGGCAAGATCCTGGAGCAGCGGAGCCTGAACA
```

-continued

CCATCCAGCAGTTTGATTACCAGAAGAAGCTGGACAACAGGGAGAAGGAG

AGGGTGGCAGCAAGGCAGGCCTGGTCTGTGGTGGGCACAATCAAGGATCT

GAAGCAGGGCTATCTGAGCCAGGTCATCCACGAGATCGTGGACCTGATGA

TCCACTACCAGGCCGTGGTGGTGCTGGAGAACCTGAATTTCGGCTTTAAG

AGCAAGAGGACCGGCATCGCCGAGAAGGCCGTGTACCAGCAGTTCGAGAA

GATGCTGATCGATAAGCTGAATTGCCTGGTGCTGAAGGACTATCCAGCAG

AGAAAGTGGGAGGCGTGCTGAACCCATACCAGCTGACAGACCAGTTCACC

TCCTTTGCCAAGATGGGCACCCAGTCTGGCTTCCTGTTTTACGTGCCTGC

CCCATATACATCTAAGATCGATCCCCTGACCGGCTTCGTGGACCCCTTCG

TGTGGAAAACCATCAAGAATCACGAGAGCCGCAAGCACTTCCTGGAGGGC

TTCGACTTTCTGCACTACGACGTGAAAACCGGCGACTTCATCCTGCACTT

TAAGATGAACAGAAATCTGTCCTTCCAGAGGGGCCTGCCCGGCTTTATGC

CTGCATGGGATATCGTGTTCGAGAAGAACGAGACACAGTTTGACGCCAAG

GGCACCCCTTTCATCGCCGGCAAGAGAATCGTGCCAGTGATCGAGAATCA

CAGATTCACCGGCAGATACCGGGACCTGTATCCTGCCAACGAGCTGATCG

CCCTGCTGGAGGAGAAGGGCATCGTGTTCAGGGATGGCTCCAACATCCTG

CCAAAGCTGCTGGAGAATGACGATTCTCACGCCATCGACACCATGGTGGC

CCTGATCCGCAGCGTGCTGCAGATGCGGAACTCCAATGCCGCCACAGGCG

AGGACTATATCAACAGCCCCGTGCGCGATCTGAATGGCGTGTGCTTCGAC

TCCCGGTTTCAGAACCCAGAGTGGCCCATGGACGCCGATGCCAATGGCGC

CTACCACATCGCCCTGAAGGGCCAGCTGCTGCTGAATCACCTGAAGGAGA

GCAAGGATCTGAAGCTGCAGAACGGCATCTCCAATCAGGACTGGCTGGCC

TACATCCAGGAGCTGCGCAACAAAAGGCCGGCGGCCACGAAAAAGGCCGG

CCAGGCAAAAAGAAAAAG.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

We claim:

1. A genome editing system comprising:
   a) a guide RNA comprising a guide segment that hybridizes with a target sequence of a DNA molecule in a eukaryotic cell to form an RNA/DNA hybrid, and wherein the guide RNA forms a stem loop 5' of the RNA/DNA hybrid, and
   b) an mRNA encoding a Cpf1 protein;
   wherein the guide RNA comprises from 15 to 50 additional nucleotides 5' of the stem loop, wherein the 15 to 50 additional nucleotides 5' of the stem loop comprises SEQ ID NO: 47, SEQ ID NO: 49, SEQ ID NO: 50, SEQ ID NO: 52, SEQ ID NO: 53, SEQ ID NO: 55, SEQ ID NO: 56, SEQ ID NO: 57, SEQ ID NO: 58, SEQ ID NO: 59, SEQ ID NO: 60, or SEQ ID NO: 61, wherein the guide RNA comprises at least three chemically modified nucleotides 5' of the stem loop, wherein the at least three chemically modified nucleotides 5' of the stem loop are a chemically modified ribose, and wherein the additional nucleotides 5' of the stem loop form a heterologous sequence;
   wherein the guide RNA comprises five chemically modified nucleotides at the 3' end of the guide segment, and wherein the five chemically modified nucleotides at the 3' end of the guide segment are a chemically modified ribose;
   wherein the guide RNA comprises a sequence selected from SEQ ID NO:2, SEQ ID NO:3, SEQ ID NO: 4, SEQ ID NO:6, SEQ ID NO:8, SEQ ID NO:9, SEQ ID NO:11, SEQ ID NO: 12, SEQ ID NO:13, SEQ ID NO:14, SEQ ID NO:15, SEQ ID NO:16, SEQ ID NO:34, SEQ ID NO: 35, SEQ ID NO:36, SEQ ID NO:37, SEQ ID NO:38, SEQ ID NO:39, SEQ ID NO: 40, SEQ ID NO: 41, SEQ ID NO: 42, SEQ ID NO: 43, SEQ ID NO: 44, and SEQ ID NO: 45; and
   wherein the chemically modified ribose comprises 2'-Fluoro (2'F).

2. The system of claim 1, wherein the guide RNA further comprises from 15 to 40 nucleotides 5' of the stem loop.

3. The system of claim 1, wherein the heterologous sequence comprises a second RNA sequence from a different species compared to the guide segment.

4. A method of RNA-guided genome editing, the method comprising: introducing into a cell:
   a) a guide RNA comprising a guide segment that hybridizes with a target sequence of a DNA molecule in a eukaryotic cell to form an RNA/DNA hybrid, and wherein the guide RNA forms a stem loop 5' of the RNA/DNA hybrid, and
   b) an mRNA encoding a Cpf1 protein;
   wherein the guide RNA comprises from 15 to 50 additional nucleotides 5' of the stem loop, wherein the 15 to 50 additional nucleotides 5' of the stem loop comprises SEQ ID NO: 47, SEQ ID NO: 49, SEQ ID NO: 50, SEQ ID NO: 52, SEQ ID NO: 53, SEQ ID NO: 55, SEQ ID NO: 56, SEQ ID NO: 57, SEQ ID NO: 58, SEQ ID NO: 59, SEQ ID NO: 60, or SEQ ID NO: 61, wherein the guide RNA comprises at least three chemically modified nucleotides 5' of the stem loop, wherein the at least three chemically modified nucleotides 5' of the stem loop area chemically modified ribose and wherein the additional nucleotides 5' of the stem loop form a heterologous sequence;

wherein the guide RNA comprises five chemically modified nucleotides at the 3' end of the guide segment, and wherein the five chemically modified nucleotide at the 3' end of the guide segment are a chemically modified ribose;

wherein the guide RNA hybridizes with the target sequence and the Cpf1 protein cleaves the DNA molecule;

wherein the guide RNA comprises a sequence selected from SEQ ID NO:2, SEQ ID NO:3, SEQ ID NO: 4, SEQ ID NO:6, SEQ ID NO:8, SEQ ID NO:9, SEQ ID NO:11, SEQ ID NO:12, SEQ ID NO:13, SEQ ID NO:14, SEQ ID NO:15, SEQ ID NO:16, SEQ ID NO:34, SEQ ID NO: 35, SEQ ID NO:36, SEQ ID NO:37, SEQ ID NO:38, SEQ ID NO:39, SEQ ID NO: 40, SEQ ID NO: 41, SEQ ID NO: 42, SEQ ID NO: 43, SEQ ID NO: 44, and SEQ ID NO: 45; and wherein the chemically modified ribose comprises 2'-Fluoro (2'F).

* * * * *